United States Patent [19]

Lattrell et al.

[11] Patent Number: 5,071,979
[45] Date of Patent: Dec. 10, 1991

[54] CEPHALOSPORIN DERIVATIVES

[75] Inventors: Rudolf Lattrell, Taunus; Manfred Wieduwilt, Frankfurt; Walter Dürckheimer, Hattersheim; Jürgen Blumbach, Frankfurt; Karl Seeger, Hofheim, all of Fed. Rep. of Germany

[73] Assignee: Hoechst Aktiengesellschaft, Frankfurt am Main, Fed. Rep. of Germany

[21] Appl. No.: 376,654

[22] Filed: May 10, 1982

[30] Foreign Application Priority Data

May 12, 1981 [DE] Fed. Rep. of Germany ....... 3118732

[51] Int. Cl.$^5$ ................ C07D 501/40; A61K 31/545
[52] U.S. Cl. ................................................. 540/225
[58] Field of Search ................. 544/25, 26, 27, 29; 424/246; 540/225

[56] References Cited

U.S. PATENT DOCUMENTS

| 4,200,746 | 4/1980 | Cook et al. ........................ 544/25 |
| 4,264,595 | 4/1981 | Numata et al. .................... 544/25 |
| 4,278,671 | 7/1981 | Ochiai et al. ..................... 544/25 |
| 4,278,793 | 4/1981 | Dürkheims et al. .............. 544/25 |
| 4,336,353 | 6/1982 | Lunn et al. ........................ 424/246 |
| 4,367,228 | 1/1983 | Takaya et al. .................... 544/25 |
| 4,379,787 | 4/1983 | Lunn et al. ........................ 544/25 |
| 4,399,131 | 8/1983 | Dürckheimer ..................... 424/246 |
| 4,501,739 | 2/1985 | Lunn et al. ........................ 544/27 |
| 4,514,565 | 4/1985 | Ochiai et al. ..................... 501/38 |
| 4,520,194 | 5/1985 | Ochiai et al. ..................... 544/25 |
| 4,609,653 | 9/1986 | Durchleimer et al. ........... 514/202 |
| 4,845,087 | 7/1989 | Lattrell et al. .................... 540/222 |

FOREIGN PATENT DOCUMENTS

| 34760 | 9/1981 | European Pat. Off. . |
| 42154 | 12/1981 | European Pat. Off. . |
| 771951 | 6/1977 | Finland . |
| 791678 | 5/1979 | Finland . |
| 801609 | 7/1979 | Finland . |
| 2094309 | 9/1982 | United Kingdom . |

Primary Examiner—Nicholas S. Rizzo

[57] ABSTRACT

What are disclosed are anti-bacterially active cephalosporin compounds of the formula

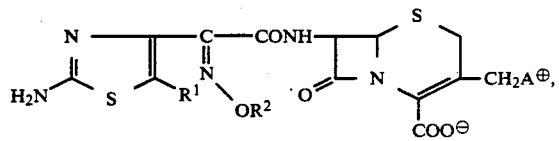

pharmaceutical preparations containing such compounds, methods of making the compounds, methods for combatting bacterial infections therewith, and intermediates for such compounds.

8 Claims, No Drawings

CEPHALOSPORIN DERIVATIVES

The present invention relates to new cephalosporin derivatives and to a process for their preparation, in particular to polar cephem derivatives which are substituted in the 3-position of the cephem ring by certain pyridiniummethyl radicals and which have a very good antimicrobial action against Gram-positive and Gram-negative bacteria and which are therefore highly suitable for use as medicaments for treating microbial infections.

The invention therefore relates to cephem derivatives of the general formula I

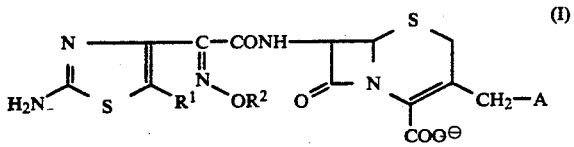

wherein $R^1$ denotes hydrogen or halogen, $R^2$ denotes hydrogen or $C_1$–$C_6$-alkyl, A denotes a pyridinium radical

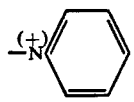

which can be monosubstituted or multisubstituted by identical or different substituents, namely by optionally substituted $C_1$–$C_6$-alkyl, of which 2 alkyl groups can be linked to form a possibly substituted di- to deca-methylene ring in which one C atom can be replaced by a heteroatom and which can additionally contain one or two double bonds, by cyano-$C_1$–$C_3$-alkyl, epoxy-$C_2$–$C_6$-alkyl, trifluoromethyl or pentafluoroethyl, by hydroxyiminomethyl or $C_1$–$C_4$-alkoxyiminomethyl, by optionally substituted $C_2$–$C_6$-alkenyl, by $C_2$–$C_6$-alkynyl, by $C_3$–$C_7$-cycloalkyl or $C_3$–$C_7$-cycloalkylmethyl, in which two substituents the ring can also be substituted, by $C_4$–$C_7$-cycloalkenyl, by optionally substituted $C_1$–$C_6$-alkoxy, by epoxy-$C_2$–$C_6$-alkoxy, by $C_2$–$C_6$-alkenyloxy or $C_2$–$C_6$-alkynyloxy, by halogen, cyano, hydroxyl or mercapto, by $C_1$–$C_6$-alkylsulfonyl, $C_1$–$C_6$-alkylsulfinyl or $C_1$–$C_6$-alkythio which is optionally substituted in the alkyl part, by methylsulfonyl, methylsulfinyl or methylthio which is substituted on the methyl radical, by $C_2$–$C_6$-alkenylthio, $C_2$–$C_6$-alkenylsulfinyl or $C_2$–$C_6$-alkenylsulfonyl, by optionally substituted phenyl, benzyl or heteroaryl, by formyl or ketalized formyl, by optionally substituted $C_1$–$C_6$-alkylcarbonyl which can also be present in ketalized form, by arylcarbonyl, by $C_1$–$C_6$-alkylcarbonylamino, by carboxyl or $C_1$–$C_6$-alkoxycarbonyl, by carbamoyl, which can be monosubstituted or disubstituted on the nitrogen, by optionally substituted carbazoyl, by sulfamoyl, which can be monosubstituted on the nitrogen, or by pyridyl or 4-pyridon-1-yl, and wherein the $R^2O$ group is in the syn position.

The present invention relates in particular to compounds in which $R^1$ and $R^2$ have the abovementioned meanings and A denotes a pyridinium radical

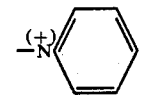

which can be 1-substituted or multisubstituted by identical or different substituents, namely by $C_1$–$C_6$-alkyl which can be monosubstituted or multisubstituted by hydroxyl, carboxyl, $C_1$–$C_6$-alkyloxycarbonyl, formyl or $C_1$–$C_6$-alkylcarbonyl, the carbonyl groups of which can also be present in ketalized form, carbamoyl, N-hydroxycarbamoyl, sulfo, $C_1$–$C_6$-alkyloxy, hydroxy-$C_1$–$C_6$-alkyloxy, $C_1$–$C_6$-alkylthio, $C_1$–$C_6$-alkylsulfinyl, $C_1$–$C_6$-alkylsulfonyl, $C_2$–$C_6$-alkenyloxy, $C_2$–$C_6$-alkenylthio, $C_2$–$C_6$-alkenylsulfinyl or $C_2$–$C_6$-alkenylsulfonyl, and of which 2 alkyl groups can also be linked to form an optionally substituted di- to deca-methylene ring in which one C atom can be replaced by one heteroatom and which can additionally contain one or two double bonds, by cyano-$C_1$–$C_3$-alkyl, epoxy-$C_2$–$C_6$-alkyl, trifluoromethyl, hydroxyiminomethyl or $C_1$–$C_4$-alkoxyiminomethyl, pentafluoroethyl, by $C_2$–$C_6$-alkenyl which can be substituted by hydroxyl, by $C_2$–$C_6$-alkynyl, by $C_3$–$C_7$-cycloalkyl or $C_3$–$C_7$-cycloalkylmethyl, in which two substituents the ring can also be substituted by hydroxyl, halogen, carboxyl, $C_1$–$C_6$-alkyloxycarbonyl or cyano, by $C_4$–$C_7$-cycloalkenyl, by $C_1$–$C_6$-alkoxy, which can be substituted by hydroxyl, carboxyl or $C_1$–$C_6$-alkyloxycarbonyl, by epoxy-$C_2$–$C_6$-alkoxy, by $C_2$–$C_6$-alkenyloxy or $C_2$–$C_6$-alkynyloxy, by halogen, cyano, hydroxyl or mercapto, by $C_1$–$C_6$-alkylthio, $C_1$–$C_6$-alkylsulfinyl or $C_1$–$C_6$-alkylsulfonyl, all of which can be substituted by hydroxyl in the alkyl part, by methylthio, methylsulfinyl or methylsulfonyl, all of which are substituted in the methyl part by carboxyl or $C_1$–$C_6$-alkyloxycarbonyl, by $C_2$–$C_6$-alkenylthio, $C_2$–$C_6$-alkenylsulfinyl or $C_2$–$C_6$-alkenylsulfonyl, by phenyl, benzyl or heteroaryl, all of which can also be substituted by halogen, by formyl or ketalized formyl, by $C_1$–$C_6$-alkylcarbonyl which can also be substituted by hydroxyl and can also be present in ketalized form, by arylcarbonyl or $C_1$–$C_6$-alkylcarbonylamino, by carboxyl or $C_1$–$C_6$-alkoxycarbonyl, by carbamoyl which can be monosubstituted on the nitrogen by $C_1$–$C_6$-alkyl, hydroxy-$C_1$–$C_6$-alkyl, $C_1$–$C_6$-alkyloxycarbonyl, $C_1$–$C_6$-alkylcarbonyl, carboxymethyl, $C_1$–$C_6$-alkyloxycarbonylmethyl, aminocarbonylmethyl, $C_1$–$C_6$-alkylaminocarbonyl, carbamoyl, hydroxyl or pyridyl, or which can be disubstituted on the nitrogen by $C_1$–$C_6$-alkyl, by carbazoyl which can be substituted by $C_1$–$C_4$-alkyl, or N-carbamoylcarbazoyl, by sulfamoyl which can be monosubstituted on the nitrogen by $C_1$–$C_6$-alkylaminocarbonyl, or by pyridyl or 4-pyridon-1-yl, and in which preferred compounds of the general formula I the $R^2O$ group is also in the syn position.

Possible substituents for the di- to deca-methylene ring mentioned under A, in which one C atom can be replaced by one heteroatom and one or two double bonds can additionally be contained, are in particular the following substituents, which can occur once or several times but preferably occur once: $C_1$–$C_6$-alkyl, $C_1$–$C_4$-alkoxy, hydroxymethyl, halogen, hydroxyl, oxo, hydroxyimino, exomethylene, carboxyl, $C_1$–$C_6$-alkyloxycarbonyl, cyano or carbamoyl.

These substituents can occur in the rings which have been mentioned and are fused onto the pyridinium radical, regardless of whether the particular ring is saturated, unsaturated or, additionally, interrupted by a heteroatom. However, according to the invention the substituents preferably occur on fused-on saturated rings which do not contain any heteroatoms.

The ring fused onto the pyridinium radical can contain 2 to 20 ring members (di- to deca-methylene), but it preferably contains 3 to 5 ring members and it can thus be, for example, a cyclopenteno, cyclohexeno or cyclohepteno ring. If such a fused-on ring contains a double bond, then the examples which may be mentioned are a dehydrocyclopenteno, dehydrocyclohexeno or dehydrocyclohepteno ring. If in such rings one C atom is replaced by one heteroatom, the latter can be in particular oxygen or sulfur. Examples which may be mentioned of fused-on rings which each contain one oxygen atom and two or one double bonds are furo, pyrano, dihydrofuro and dihydropyrano, and examples of fused-on rings which each have one sulfur atom and contain two or one double bonds are thieno, thiopyrano, dihydrothieno and dihydrothiopyrano. Among the fused-on rings which each contain one heteroatom, candidates for a substitution, in particular by the abovementioned substituents, are in particular those rings which contain only one double bond.

Examples of particularly preferable substituents are: $R^1$: hydrogen, chlorine and fluorine, in particular chlorine, $R^2$: hydrogen, $C_1$–$C_4$-alkyl, such as, for example, methyl, ethyl, propyl, isopropyl, preferably methyl, ethyl, in particular methyl, A: a pyridinium radical which can be monosubstituted or multisubstituted, preferably 1- to 3-fold, in particular 1- to 2-fold, for example by $C_1$–$C_4$-alkyl, such as, in particular, methyl, ethyl, propyl, isopropyl, n-butyl, sec.-butyl, tert.-butyl, dimethyl, trimethyl, methyl and ethyl, methyl and propyl, methyl and isopropyl, ethyl and ethyl, hydroxy-$C_1$–$C_4$-alkyl, such as in particular, hydroxymethyl, hydroxyethyl, hydroxypropyl, hydroxyisopropyl, hydroxybutyl, hydroxy-sec.-butyl or hydroxy-tert.-butyl, and in which it is also possible for the alkyl radical to be substituted by two or three hydroxyl groups, carboxy-$C_1$–$C_4$-alkyl, such as, in particular, carboxymethyl and carboxyethyl, $C_1$–$C_4$-alkyloxycarbonyl-$C_1$–$C_4$-alkyl, such as, in particular, methyloxycarbonylmethyl, ethyloxycarbonylmethyl, methyloxycarbonylethyl, formyl-$C_1$–$C_4$-alkyl, such as, in particular, formylmethyl, $C_1$–$C_4$-alkylcarbonyl-$C_1$–$C_4$-alkyl, such as, in particular, methylcarbonylmethyl, ethylcarbonylmethyl, methylcarbonylethyl and ethylcarbonylethyl, the two alkyl groups of which can also be further substituted by hydroxyl and the carbonyl group of which can also be present in the ketalized form, carbamoyl-$C_1$–$C_4$-alkyl, such as, in particular, carbamoylmethyl and carbamoylethyl, which can also be further substituted by hydroxyl on the nitrogen, such as, in particular, N-hydroxycarbamoylmethyl, sulfo-$C_1$–$C_4$-alkyl, such as, in particular, sulfoethyl or 1-hydroxy-1-sulfomethyl, $C_1$–$C_4$-alkyloxy-$C_1$–$C_4$-alkyl, such as, in particular, methoxymethyl, ethoxymethyl, propoxymethyl, isopropoxymethyl, methoxyethyl, ethoxyethyl, methoxypropyl and methoxyisopropyl, all of which can be substituted by hydroxyl, such as, in particular, hydroxyethoxymethyl and hydroxyethoxyethyl, $C_1$–$C_4$-alkylthio-$C_1$–$C_4$-alkyl, such as, in particular, methylthiomethyl, ethylthiomethyl, methylthioethyl and ethylthioethyl, $C_1$–$C_4$-alkylsulfinyl-$C_1$–$C_4$-alkyl, such as, in particular, methylsulfinylmethyl, ethylsulfinylmethyl, methylsulfinylethyl and ethylsulfinylethyl, $C_1$–$C_4$-alkylsulfonyl-$C_1$–$C_4$-alkyl, such as, in particular, methylsulfonylmethyl, ethylsulfonylmethyl, methylsulfonylethyl and ethylsulfonylethyl, $C_3$-alkenyloxy-$C_1$–$C_4$-alkyl, such as, in particular, allyloxymethyl and allyloxyethyl, $C_3$-alkenylthio-$C_1$–$C_4$-alkyl, such as, in particular, allylthiomethyl, $C_3$-alkenylsulfinyl-$C_1$–$C_4$-alkyl, such as, in particular, allylsulfinylmethyl, $C_3$-alkenylsulfonyl-$C_1$–$C_4$-alkyl, such as, in particular, allylsulfonylmethyl, cyano-$C_1$–$C_3$-alkyl, such as, in particular, cyanomethyl and cyanoethyl, epoxy-$C_2$–$C_3$-alkyl, such as, in particular, epoxyethyl and epoxypropyl, trifluoromethyl, hydroxyiminomethyl and $C_1$–$C_3$-alkoxyiminomethyl, such as, in particular, methoxyiminomethyl, $C_3$–$C_4$-alkenyl, such as, in particular, allyl, 2-methylallyl and buten-3-yl, all of which can also be further substituted by hydroxyl, such as, in particular, hydroxyallyl and hydroxybutenyl, $C_3$-alkynyl, such as, in particular, propargyl, $C_3$–$C_6$-cycloalkyl and $C_3$–$C_6$-cycloalkylmethyl, in which the number of carbons relates to the cycloalkyl part, such as, in particular, cyclopropyl, cyclobutyl, cyclopentyl, cyclohexyl and cyclopentylmethyl, in which the rings can also be substituted, for example, by hydroxyl, such as, in particular, 1-hydroxy-1-cyclopentyl and 1-hydroxy-1-cyclohexyl, or by halogen, preferably chlorine, by carboxyl, $C_1$–$C_4$-alkoxycarbonyl or cyano, $C_5$–$C_6$-cycloalkenyl, such as, in particular, cyclopenten-1-yl and cyclohexen-1-yl, $C_1$–$C_4$-alkoxy, such as, in particular, methoxy, ethoxy, propoxy, isopropoxy, butoxy, isobutoxy and tert.-butoxy, preferably methoxy, all of which alkoxy groups can also be further substituted, for example, by hydroxyl, carboxyl or $C_1$–$C_4$-alkoxycarbonyl, in particular carboxymethoxy and methoxycarbonylmethoxy, epoxy-$C_2$–$C_3$-alkoxy, such as, in particular, epoxyethoxy or epoxypropoxy, $C_3$-alkenyloxy, such as, in particular, allyloxy, $C_3$-alkynyloxy, such as, in particular, propargyloxy, halogen, such as, in particular, fluorine, chlorine, bromine or iodine, cyano, hydroxyl, in particular 3-hydroxy, $C_1$–$C_4$-alkylthio, such as, in particular, methylthio, ethylthio, propylthio and isopropylthio, all of which can also be substituted by hydroxyl, in particular hydroxyethylthio, $C_1$–$C_4$-alkylsulfinyl, such as, in particular, methylsulfinyl, ethylsulfinyl, propylsulfinyl and isopropylsulfinyl, all of which can also be substituted by hydroxyl, in particular hydroxyethylsulfinyl, $C_1$–$C_4$-alkylsulfonyl, such as methylsulfonyl, ethylsulfonyl, propylsulfonyl or isopropylsulfonyl, all of which can also be substituted by hydroxyl, in particular hydroxyethylsulfonyl, carboxymethylthio and $C_1$–$C_4$-alkoxycarbonylmethylthio, in particular methoxycarbonylmethylthio, carboxymethylsulfinyl and carboxymethylsulfonyl, $C_1$–$C_4$-alkoxycarbonylmethylsulfinyl and -alkoxycarbonylmethylsulfonyl, in particular methoxycarbonylmethylsulfinyl and methoxycarbonylmethylsulfonyl, $C_3$-alkenylthio, such as allylthio and propen-1-ylthio, $C_3$-alkenylsulfinyl, such as allylsulfinyl and propen-1-ylsulfinyl, $C_3$alkenylsulfonyl, such as allylsulfonyl and propen-1-ylsulfonyl, phenyl and benzyl, both of which can also be substituted, for example by halogen, in particular chlorine, such as, for example, 4-chlorobenzyl, 2'-thienyl and 3'-thienyl, formyl and ketalized formyl, such as, for example, 1,3-dioxolan-2-yl, $C_1$–$C_4$-alkylcarbonyl, in particular acetyl and propionyl, preferably acetyl, which can also be substituted by hydroxyl and be present in ketalized form, such as, for example, 2-methyl-1,3-dioxolan-2-yl, benzoyl, $C_1$–$C_4$-alkylcarbonylamino, in particular acetylamino and propionylamino, formylamino, carboxyl, for example also 2,3,4-carboxy, $C_1$–$C_4$-alkoxycarbonyl, in particular methoxycarbonyl and ethoxycarbonyl, such as, for example, also 2,3,4-methoxycarbonyl or 2,3,4-ethoxycarbonyl, carbamoyl (for example also 2,3,4-carbamoyl) which can be monosubstituted on the nitrogen atom by $C_1$–$C_4$-alkyl, such as, in particular, N-methylcarbamoyl and N-ethylcarbamoyl, by hydroxy-$C_1$–$C_4$-alkyl, such as, in particular, N-hydroxymethylcarbamoyl and N-hydroxyethylcarbamoyl, by $C_1$–$C_4$-alkoxycarbonyl, such as, in particular, N-methoxycarbonylcarbamoyl and N-ethoxycarbonylcarbamoyl, by $C_1$–$C_4$-alkylcarbonyl, such as, in particular, N-acetylcarbamoyl, by carboxymethyl, by $C_1$–$C_4$-alkoxycarbonylmethyl, such as, in particular, N-methoxycarbonylmethylcarbamoyl and N-ethoxycarbonylmethylcarbamoyl, by aminocarbonylmethyl, by N-$C_1$–$C_4$-alkylaminocarbonyl, such as, in particular, N-methylaminocarbonylcarbamoyl and N-ethylaminocarbonylcarbamoyl, by carbamoyl (=ureidocarbonyl), by hydroxyl or pyridyl, such as, in particular, N-3'-pyridylcarbamoyl and N-4'-pyridylcarbamoyl, N-$C_1$–$C_4$-dialkylcarbamoyl, such as, in particular, N,N-dimethylcarbamoyl and N,N-diethylcarbamoyl, carbazoyl which can be substituted by $C_1$–$C_4$-alkyl, in particular methyl or ethyl, by carbamoyl, such as N-carbamoylcarbazoyl, sulfamoyl, which can be substituted on the nitrogen atom by $C_1$–$C_4$-alkylaminocarbonyl, such as, in particular, ethylaminocarbonylsulfamoyl, and pyridyl, such as, in particular, 2'-, 3'- and 4'-pyridyl and 4-pyridon-1-yl.

If A represents a pyridinium radical which is substituted by two alkyl groups which are linked to form a di- to deca-methylene ring which in turn can be monosubstituted or multisubstituted but preferably is monosubstituted and can contain one or two double bonds, examples of this are in particular the following fused-on ring systems: cyclopenteno, hydroxycyclopenteno, chlorocyclopenteno, bromocyclopenteno, oxocyclopenteno, hydroxymethylcyclopenteno, exomethylenecyclopenteno, carboxycyclopenteno, $C_1$–$C_4$-alkoxycarbonylcyclopenteno, in particular methoxycarbonylcyclopenteno and carbamoylcyclopenteno, cyclohexeno, hydroxycyclohexeno, chlorocyclohexeno, bromocyclohexeno, oxocyclohexeno, hydroxymethylcyclohexeno, exomethylenecyclohexeno, carboxycyclohexeno, $C_1$–$C_4$-alkoxycarbonylcyclohexeno, in particular methoxycarbonylcyclohexeno and carbamoylcyclohexeno, cyclohepteno, hydroxy-, chloro-, bromo-, oxo-, hydroxymethyl-, exomethylene- or carboxycyclohepteno, in particular methoxycarbonylcyclohepteno and carbamoylcyclohepteno, dehydrocyclopenteno, dehydrocyclohexeno and dehydrocyclohepteno.

If in the abovementioned fused-on ring systems one C atom is replaced by one heteroatom, in particular oxygen or sulfur, possible examples are in particular: 2,3- and 3,4-furo, 2,3- and 3,4-pyrano, 2,3- and 3,4-dihydrofuro, 2,3- and 3,4-dihydropyrano, methyldihydrofuro, methoxydihydropyrano and hydroxydihydropyrano.

The invention also relates to a process for preparing compounds of the formula I and their physiologically acceptable acid addition salts, which process comprises reacting a) a compound of the general formula II

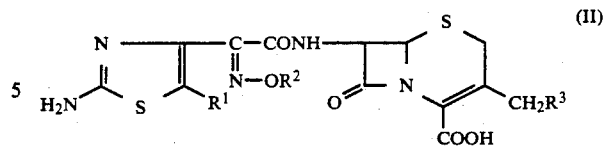

or its salts, wherein $R^1$ and $R^2$ have the abovementioned meaning and $R^3$ denotes a group which can be replaced by pyridine or substituted pyridines which correspond to the pyridinium radicals A of the formula I, with pyridine or such a pyridine derivative or b) reacting a 7-aminocephem compound of the general formula III

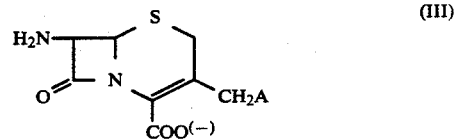

or its acid addition salts, in which the amino group can also be present in the form of a reactive derivative, with a 2-(2-aminothiazol-4-yl)-2-syn-oximinoacetic acid of the general formula IV

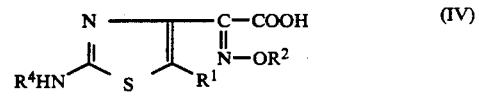

wherein $R^1$ and $R^2$ have the above meaning and $R^4$ represents hydrogen or an amino protective group or with an activated derivative of this compound and α) eliminating a protective group, if present, and β) if necessary, converting the product obtained into a physiologically acceptable acid addition salt.

If the compounds of the general formula I are to be prepared by a nucleophilic replacement reaction of $R^3$ in the compounds of the general formula II by pyridine or one of the pyridine derivatives indicated, possible examples of radicals $R^3$ are in particular acyloxy radical of lower aliphatic carboxylic acids, preferably having 1 to 4 C atoms, such as, for example, acetoxy or propionyloxy, in particular acetoxy, which radicals may be substituted, such as, for example, chloroacetoxy or acetylacetoxy. Other groups are also possible for $R^3$ such as, for example, halogen, in particular chlorine or bromine, or carbamoyloxy.

Starting compounds of the general formula II in which $R^3$ represents acetoxy, or their salts, such as, for example, a sodium salt or potassium salt, are used, according to the invention, in the nucleophilic replacement reaction. The reaction is carried out in a solvent, preferably in water, or in a mixture of water and an organic solvent which is readily miscible with water, such as, for example, acetone, dioxane, acetonitrile, dimethylformamide, dimethylsulfoxide or ethanol. The reaction temperature is in general within the range from about 10° to about 100° C., preferably between 20° and 80° C. The pyridine component is added in amounts which are between approximately equimolar amounts and not more than an approximately 5-fold excess. The replacement of the radical $R^3$ is facilitated by the presence of neutral salt ions, preferably of iodide or thiocyanate ions, in the reaction medium. In particular, about 10 to about 30 equivalents of potassium iodide, sodium iodide, potassium thiocyanate or sodium thiocyanate are added. The reaction is advantageously carried out under approximately neutral conditions, preferably at a pH value within the range from about 5 to about 8.

If $R^3$ represents a carbamoyloxy group, the replacement reaction is carried out analogously. If $R^3$ represents halogen, in particular bromine, the replacement is effected in a manner described in the literature.

The acylation of the compounds of the general formula III or of their addition salts, for example with hydrochloric acid, hydrobromic acid, nitric acid, phosphoric acid or an organic acid, such as, for example, methanesulfonic acid or p-toluenesulfonic acid, can be carried out by means of carboxylic acids of the general formula IV or by means of a reactive derivative of such an acid. In this step, it is in some cases advantageous to protect the 2-amino group in the compounds of the general formula IV from the reaction. Suitable examples of amino protective groups $R^4$ are optionally substituted alkyl, such as, for example, tert.-butyl, tert.-amyl, benzyl, p-methoxybenzyl, trityl, benzhydryl, preferably trityl, trialkylsilyl, such as, for example, trimethylsilyl, optionally substituted aliphatic acyl, such as, for example, formyl, chloroacetyl, bromoacetyl, trichloroacetyl and trifluoroacetyl, preferably chloroacetyl, or optionally substituted alkoxycarbonyl, such as, for example, trichloroethoxycarbonyl, benzyloxycarbonyl or tert.-butoxycarbonyl, preferably tert.-butoxycarbonyl and benzyloxycarbonyl.

After the acylation, the protective group can be split off in a manner which is in itself known, for example the trityl group by means of a carboxylic acid, such as, for example acetic acid or formic acid, or the chloroacetyl group by means of thiourea.

If the carboxylic acids of the general formula IV and their derivatives protected at the amino group are themselves used as acylating agents, the reaction is advantageously carried out in the presence of a condensing agent, for example of a carbodiimide, such as, for example, N,N'-dicyclohexylcarbodiimide.

The activation of the carboxylic acids of the general formula IV can be particularly advantageously effected by treatment with certain carboxamides and, for example, phosgene, phosphorus pentachloride, tosyl chloride, thionyl chloride or oxalyl chloride, as described in German Patent 2,804,040.

Suitable activated derivatives of the carboxylic acids of the general formula IV are in particular also halides, preferably chlorides, which can be obtained in a manner which is in itself known by treatment with halogenating agents, such as, for example, phosphorus pentachloride, phosgene or thionyl chloride, under mild reaction conditions described in cephalosporin chemistry literature.

Further suitable activated derivatives of the carboxylic acids of the general formula IV are the anhydrides and mixed anhydrides, azides and activated esters, preferably those formed with p-nitrophenol, 2,4-dinitrophenol, methylenecyanohydrin, N-hydroxysuccinimide and N-hydroxyphthalimide, in particular those formed with 1-hydroxybenzotriazole and 6-chloro-1-hydroxybenzotriazole. Particularly suitable mixed anhydrides are those formed with lower alkanoic acids, such as, for example, acetic acid, and particularly preferably those formed with substituted acetic acids, such as, for example, trichloroacetic acid, pivalic acid or cyanoacetic acid. However, those mixed anhydrides are also particularly suitable which are formed with carbonic acid half-esters, which are obtained, for example, by reacting the carboxylic acids of the formula IV, in which the amino group is protected, with benzyl chloroformate, p-nitrobenzyl chloroformate, isobutyl chloroformate, ethyl chloroformate or allyl chloroformate. The activated derivatives can be reacted as isolated substances or in situ.

Generally, the reaction of the cephem derivatives of the general formula III with a carboxylic acid of the general formula IV or with an activated derivative thereof is carried out in the presence of an inert solvent. Particularly suitable solvents are chlorinated hydrocarbons, such as, for example, methylene chloride and chloroform, ethers, such as, for example, diethyl ether, preferably tetrahydrofuran and dioxan, ketones, such as preferably acetone and butanone, amides, such as preferably dimethylformamide and dimethylacetamide, or water. It can also be advantageous to use mixtures of the solvents mentioned. This can be advantageous in many cases where the cephem compound of the general formula III is reacted with an activated derivative of a carboxylic acid of the formula IV which derivative has been formed in situ.

The reaction of cephem compounds of the formula III with carboxylic acids of the formula IV or with activated derivatives thereof can be carried out within a temperature range of about $-80°$ to about $+80°$ C., preferably between $-30°$ and $+50°$ C., but in particular between about $-20°$ C. and room temperature.

The reaction time depends on the reactants, the temperature and the solvent or the mixture of solvents and normally is between about $\frac{1}{4}$ and about 72 hours.

The reaction with acid-halides may be carried out in the presence of an acid-binding agent to bind the hydrogen halide liberated. Suitable acid-binding agents are in particular tertiary amines, such as, for example, triethylamine or dimethylaniline, inorganic bases, such as, for example, potassium carbonate or sodium carbonate, or alkylene oxides, such as, for example, propylene oxide. The presence of a catalyst, such as, for example, of dimethylaminopyridine, may also be advantageous.

If in the compounds of the general formula III the amino group is present in the form of a reactive derivative, the latter can be of a type described in the literature for amidation. Possible examples are thus silyl derivatives which are formed when compounds of the general formula III are reacted with a silyl compound, such as, for example, trimethylsilylchlorosilane or bis-(trimethylsilyl)-acetamide. If the reaction is carried out with one of these compounds which are activated at the amino group, it is advantageous to carry out the reaction in an inert solvent, such as, for example, methylene chloride, tetrahydrofuran or dimethylformamide.

Physiologically acceptable acid addition salts of compounds of the general formula I which may be mentioned by way of example are those salts formed with hydrochloric acid, hydrobromic acid, nitric acid, phosphoric acid or with organic acids, such as, for example, methanesulfonic acid or p-toluenesulfonic acid.

Compounds of the general formula III can be obtained in a manner which is in itself known (cf, for example, German Offenlegungsschrift 3,019,838), for example from 7-aminocephalosporanic acid protected at the amino group, in the same way as described above for the nucleophilic replacement of $R^3$.

Compounds of the general formula IV and the pyridine derivatives which correspond to the pyridinium radicals A are known from the literature or can be prepared by methods described in the literature.

Compounds of the general formula I, obtained according to the invention, and their physiologically acceptable acid addition salts have remarkably high antibacterial actions, not only against Gram-positive but also against Gram-negative bacterial germs.

The compounds of the formula I are also unexpectedly highly active against penicillinase- and cephalosporinase-forming bacteria. Since these compounds additionally have favorable toxicological and pharmacological properties, they are valuable chemotherapeutic agents.

The invention thus also relates to medicaments for treating microbial infections and which contain one or more of the compounds according to the invention.

The products according to the invention can also be used in combination with other active compounds, for example of the series of the penicillins, cephalosporins or aminoglycosides.

The compounds of the general formula I and their physiologically acceptable acid addition salts can be administered orally, intramuscularly or intravenously. Medicaments which contain one or more compounds of the general formula I as active compound can be prepared by mixing the compounds of the formula I with one or more pharmacologically acceptable excipients or diluents, such as, for example, fillers, emulsifiers, lubricants, taste corrigents, colorants or buffer substances and bringing the mixtures into a suitable galenic administration form, such as, for example, tablets, coated tablets, capsules or a solution or suspension suitable for parenteral administration.

Examples which may be mentioned of excipients or diluents are tragacanth, lactose, talc, agar-agar, polyglycols, ethanol and water. Preferably suspensions or solutions in water are used for parenteral administration. It is also possible to administer the active compounds as such, without excipients or diluents, in a suitable form, for example in capsules.

Suitable doses of compounds of the general formula I or of their physiologically acceptable acid addition salts are from about 0.4 to 20 g per day, preferably 0.5 to 4 g per day, for an adult weighing about 60 kg.

Single, or in general, multiple doses can be administered, and the single dose can contain the active compound in an amount from about 50 to 1,000 mg, preferably from about 100 to 500 mg.

Cephem compounds which carry a substituted pyridiniummethyl radical in the 3-position of the cephem ring are known from German Offenlegungsschriften 2,921,316, 2,716,707 and 2,715,385.

In addition to the products described in the illustrative examples it is also possible to prepare, according to the invention, compounds which correspond, for example, to the general formula I'

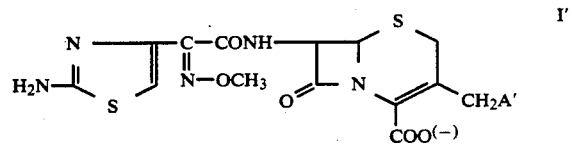

in which —OCH$_3$ is in the syn position and A' represents a) a pyridinium radical which is substituted by radicals indicated in Table 1 or b) a radical shown in Table 2.

In Table 1, the numbers show the position of the substituent(s) on the pyridinium radical.

TABLE 1

| | | |
|---|---|---|
| 2,3-di-CH$_3$ | 3-Cyclobutyl | 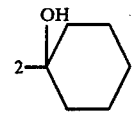 2-OH-cyclohexyl |
| 2,5-di-CH$_3$ | 4-Cyclobutyl | |
| 2-Propyl | 2-Cyclopentyl | |
| 3-Propyl | 3-Cyclopentyl | |
| 2-Isopropyl | 4-Cyclopentyl | 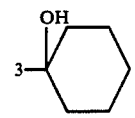 3-OH-cyclohexyl |
| 2-n-Butyl | 2-Cyclopentylmethyl | |
| 3-n-Butyl | 3-Cyclopentylmethyl | |
| 4-n-Butyl | 4-Cyclopentylmethyl | 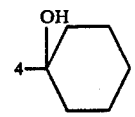 4-OH-cyclohexyl |
| 2-sec-Butyl | 2-Cyclohexyl | |
| 3-sec-Butyl | 3-Cyclohexyl | |
| 4-sec-Butyl | 4-Cyclohexyl | 2-CH$_2$OH-3-CH$_3$ |
| 2-tert-Butyl | 2-Cyclopentyl-3-CH$_3$ | 2-CH$_2$OH-4-CH$_3$ |
| 3-tert-Butyl | 2-Cyclopentyl-4-CH$_3$ | 2-CH$_2$OH-5-CH$_3$ |
| 2-C$_2$H$_5$-3-CH$_3$ | 2-Cyclopentyl-5-CH$_3$ | 3-CH$_2$OH-2-CH$_3$ |
| 2-C$_2$H$_5$-4-CH$_3$ | 3-Cyclopentyl-4-CH$_3$ | 3-CH$_2$OH-4-CH$_3$ |
| 2-C$_2$H$_5$-5-CH$_3$ | 3-Cyclopentyl-5-CH$_3$ | 3-CH$_2$OH-5-CH$_3$ |
| 3-C$_2$H$_5$-2-CH$_3$ | 4-Cyclopentyl-2-CH$_3$ | 3-CH$_2$OH-6-CH$_3$ |
| 3-C$_2$H$_5$-5-CH$_3$ | 4-Cyclopentyl-3-CH$_3$ | 4-CH$_2$OH-2-CH$_3$ |
| 4-C$_2$H$_5$-2-CH$_3$ | 2-(1-Cyclopenten-1-yl) | 4-CH$_2$OH-3-CH$_3$ |
| 4-C$_2$H$_5$-3-CH$_3$ | 3-(1-Cyclopenten-1-yl) | 2-CH$_2$OH-3-C$_2$H$_5$ |
| 2,3,4-triCH$_3$ | 4-(1-Cyclopenten-1-yl) | 2-CH$_2$OH-4-C$_2$H$_5$ |
| 2,3,5-triCH$_3$ | 2-(1-Cyclohexen-1-yl) | 2-CH$_2$OH-5-C$_2$H$_5$ |
| 2,4,5-triCH$_3$ | 3-(1-Cyclohexen-1-yl) | 3-CH$_2$OH-2-C$_2$H$_5$ |
| 3,4,5-triCH$_3$ | 4-(1-Cyclohexen-1-yl) | 3-CH$_2$OH-4-C$_2$H$_5$ |
| 2-CH$_2$CH=CH$_2$ | 2-CH$_2$C≡CH | 3-CH$_2$OH-5-C$_2$H$_5$ |
| 3-CH$_2$CH=CH$_2$ | 3-CH$_2$C≡CH | 3-CH$_2$OH-6-C$_2$H$_5$ |
| 4-CH$_2$CH=CH$_2$ | 4-CH$_2$C≡CH | 4-CB$_2$OH-2-C$_2$H$_5$ |

TABLE 1-continued

| | | |
|---|---|---|
| 2-CH₂CH₂CH=CH₂ | (2-hydroxycyclopentyl) | 4-CH₂OH-3-C₂H₅ |
| 3-CH₂CH₂CH=CH₂ | | 2-CH₂OH-3,4-diCH₃ |
| 4-CH₂CH₂CH=CH₂ | | 2-CH₂OH-3,5-diCH₃ |
| 2-CH₂C(CH₃)=CH₂ | (3-hydroxycyclopentyl) | 2-CH₂OH-4,5-diCH₃ |
| 3-CH₂C(CH₃)=CH₂ | | 3-CH₂OH-2,4-diCH₃ |
| 4-CH₂C(CH₃)=CH₂ | | 3-CH₂OH-2,5-diCH₃ |
| 2-Cyclopropyl | | 3-CH₂OH-4,5-diCH₃ |
| 3-Cyclopropyl | (4-hydroxycyclopentyl) | 3-CH₂OH-4,6-diCH₃ |
| 4-Cyclopropyl | | 3-CH₂OH-5,6-diCH₃ |
| 2-Cyclobutyl | | 4-CH₂OH-2,3-diCH₃ |
| 4-CH₂OH-2,5-diCH₃ | 2-CH₂CH(OH)CH₃-4-CH₃ | 3-CHCH₂CH=CH₂ |
| 4-CH₂OH-5,6-diCH₃ | 2-C(CH₃)₂OH-4-CH₃ |    | |
| 3-CH₂OH-4,5,6-triCH₃ | 3-C(CH₃)₂OH-6-CH₃ |   OH |
| 2-CH₂CH₂OH | 4-C(CH₃)₂OH-3-CH₃ | 4-CHCH₂CH=CH₂ |
| 3-CH₂CH₂OH | 2-CH(CH₃)OH-4-C₂H₅ |    | |
| | |   OH |
| 4-CH₂CH₂OH | 2-CH₂CH₂OH-5-C₂H₅ | 2,3-di-CH₂OH |
| 2-CH₂CH₂OH-4-CH₃ | 3-CH(CH₃)OH-2,5-diCH₃ | 2,5-di-CH₂OH |
| 2-CH₂CH₂OH-3-CH₃ | 4-CH₂CH₂OH-3,5-diCH₃ | 2,4-di-CH₂OH |
| 2-CH₂CH₂OH-5-CH₃ | 2-CH(C₃H₇)OH | 3,4-di-CH₂OH |
| 3-CH₂CH₂OH-2-CH₃ | 3-CH(C₃H₇)OH | 3,5-di-CH₂OH |
| 3-CH₂CH₂OH-4-CH₃ | 4-CH(C₃H₇)OH | 2-CH₂OH-3-OH |
| 3-CH₂CH₂OH-5-CH₃ | 2-CH(C₂H₅)CH₂OH | 2-CH₂OH-3-OH-6-CH₃ |
| 3-CH₂CH₂OH-6-CH₃ | 3-CH(C₂H₅)CH₂OH | 2-CH-(CH₂OH)₂ |
| 4-CH₂CH₂OH-3-CH₃ | 4-CH(C₂H₅)CH₂OH | 3-CH(CH₂OH)₂ |
| 4-CH₂CH₂OH-2-CH₃ | 2-CH₂(CH₂)₃OH | 4-CH(CH₂OH)₂ |
| 2-CH(CH₃)OH-3-CH₃ | 3-CH₂(CH₂)₃OH | 3-C(CH₂OH)₃ |
| 2-CH(CH₃)OH-4-CH₃ | 4-CH₂(CH₂)₃OH | 4-C(CH₂OH)₃ |
| 2-CH(CH₃)OH-5-CH₃ | 2-CH(CH₃)CH₂CH₂OH | 2-CHOHCH₂OH |
| 3-CH(CH₃)OH-2-CH₃ | 3-CH(CH₃)CH₂CH₂OH | 3-CHOHCH₂OH |
| 3-CH(CH₃)OH-4-CH₃ | 4-CH(CH₃)CH₂CH₂OH | 4-CHOHCH₂OH |
| 3-CH(CH₃)OH-5-CH₃ |     CH₃ | 2-COCH₂OH |
| 3-CH(CH₃)OH-6-CH₃ |     | | 3-COCH₂OH |
| 4-CH(CH₃)OH-2-CH₃ | 2-C(C₂H₅)OH | 4-COCH₂OH |
| 4-CH(CH₃)OH-3-CH₃ |     CH₃ | 4-C(CH₂OH)(O-CH₂-O) (dioxolane) |
| 2-CH(C₂H₅)OH |     | | |
| 3-CH(C₂H₅)OH | 3-C(C₂H₅)OH | |
| 4-CH(C₂H₅)OH |     CH₃ | 3-CH₂COCH₃ |
| |     | | 2-CH₂COCH₃ |
| | 4-C(C₂H₅)OH | |
| 2-CH(CH₃)CH₂OH | 2-CH₂C(CH₃)₂OH | 4-CH₂COCH₃ |
| 3-CH(CH₃)CH₂OH | 3-CH₂C(CH₃)₂OH | 4-CH₂C(CH₃)(O-CH₂-O) (dioxolane) |
| 4-CH(CH₃)CH₂OH | 4-CH₂C(CH₃)₂OH | |
| 4-CH(CH₃)CH₂OH-5-CH₃ | 4-C(=CH₂)CH₂OH | |
| 2-(CH₂)₃OH | 3-C(=CH₂)CH₂OH | 3-CHCH₂COCH₃ |
| 3-(CH₂)₃OH | 2-C(=CH₂)CH₂OH |    | |
| | |   OH |
| 4-(CH₂)₃OH | 4-CH(OH)CH=CH₂ | 4-CHCH₂COCH₃ |
| 2-CH₂CH(OH)CH₃ | 2-CH(OH)CH=CH₂ |    | |
| | |   OH |
| 3-CH₂CH(OH)CH₃ | 3-CH(OH)CH=CH₂ | 4-CH—COCH₃ |
| 4-CH₂CH(OH)CH₃ | 2-CH(OH)CH₂CH=CH₂ |    | |
| | |   OH |

TABLE 1-continued

| | | |
|---|---|---|
| 2-CH(O-O) | 2-OCH₃<br>2-OCH₃ | 2-butoxy<br>3-butoxy |
| 3-CH(O-O) | 2-OCH₃-3-CH₃<br>2-OCH₃-4-CH₃<br>2-OCH₃-5-CH₃ | 4-butoxy<br>4-butoxy-2-CH₃<br>2-Isobutoxy |
| 4-CH(O-O) | 3-OCH₃-2-CH₃<br>3-OCH₃-4-CH₃ | 3-Isobutoxy<br>4-Isobutoxy |
| 2-C(O-O)(CH₃) | 3-OCH₃-5-CH₃<br>3-OCH₃-6-CH₃<br>4-OCH₃-2-CH₃ | 2-tert butoxy<br>3-tert butoxy<br>4-tert butoxy |
| 3-C(O-O)(CH₃) | 4-OCH₃-3-CH₃<br>2-OC₂H₅<br>3-OC₂H₅ | 2-OCH₂—CH=CH₂<br>3-OCH₂—CH=CH₂<br>4-O—CH₂—CH=CH₂ |
| 4-C(O-O)(CH₃) | 4-OC₂H₅<br>2-OC₂H₅-3-CH₃<br>2-OC₂H₅-4-CH₃<br>2-OC₂H₅-5-CH₃ | 2-OCH₂CH₂OH<br>3-OCH₂CH₂OH<br>4-OCH₂CH₂OH<br>2-CH₂—OCH₃ |
| 4-CH(O)CH₂ (epoxide) | 3-OC₂H₅-2-CH₃<br>3-OC₂H₅-4-CH₃ | 3-CH₂—OCH₃<br>3-CH₂OCH₃—2CH₃ |
| 3-CH(O)CH₂ (epoxide) | 3-OC₂H₅-5-CH₃<br>3-OC₂H₅-6-CH₃ | 2-CH₂OC₂H₅<br>3-CH₂OC₂H₅ |
| 3-OCH₂—C(O)CH₂ | 4-OC₂H₅-2-CH₃<br>4-OC₂H₅-3-CH₃ | 4-CH₂OC₂H₅<br>2-CH₂OC₃H₇ |
| 4-OCH₂—C(O)CH₂ | 2-OCH₃-4-C₂H₅<br>4-OCH₃-2,5-diCH₃<br>2-OCH(CH₃)₂ | 3-CH₂OC₃H₇<br>4-CH₂OC₃H₇<br>2-CH₂OCH(CH₃)₂ |
| 4-CH₂CHO<br>3-CH₂CHO<br>2-CH₂CHO | 3-OCH(CH₃)₂<br>4-OCH(CH₃)₂<br>4-OCH(CH₃)₂-2-CH₃ | |
| 4-CH₂CH(O-O) (dioxolane) | | |
| 3-CH₂CH(O-O) (dioxolane) | | |
| 2-CH₂CH(O-O) (dioxolane) | | |
| 3-CH₂OCH(CH₃)₂<br>4-CH₂OCH(CH₃)₂<br>2-CH₂OCH₂CH=CH₂<br>3-CH₂OCH₂CH=CH₂<br>4-CH₂OCH₂CH=CH₂<br>2-CH₂CH₂OCH=CH₂ | 3-OH-2-CH₃<br>3-OH-4-CH₃<br>3-OH-5-CH₃<br>3-OH-6-CH₃<br>3-OH-2-C₂H₅-5-CH₃<br>3-OH-5-C₂H₅-2-CH₃ | 3-SOCH₃<br>4-SOCH₃<br>2-SO₂CH₃<br>3-SO₂CH₃<br>4-SO₂CH₃<br>2-SO₂H₅ |

TABLE 1-continued

| | | |
|---|---|---|
| 3-CH$_2$CH$_2$OCH=CH$_2$ | 3-OH-2-HC(CH$_3$)$_2$ | 3-SC$_2$H$_5$ |
| 4-CH$_2$CH$_2$OCH=CH$_2$ | 3-OH-2-CH$_2$CH$_2$CH$_3$ | 4-SC$_2$H$_5$ |
| 2-CH$_2$CH$_2$OCH$_3$ | 3-OH-2-butyl | 2-SOC$_2$H$_5$ |
| 3-CH$_2$CH$_2$OCH$_3$ | 3-OH-2-secbutyl | 3-SOC$_2$H$_5$ |
| 4-CH$_2$CH$_2$OCH$_3$ | 3-OH-2-tert.butyl | 4-SOC$_2$H$_5$ |
| 3-CH$_2$CH$_2$OCH$_3$-4-CH$_3$ | 3-OH-4-butyl | 2-SO$_2$C$_2$H$_5$ |
| 2-CH$_2$CH$_2$OC$_2$H$_5$ | 3-OH-5-sec.butyl | 3-SO$_2$C$_2$H$_5$ |
| 3-CH$_2$CH$_2$OC$_2$H$_5$ | 3-OH-2,4,5-tri-CH$_3$ | 4-SO$_2$C$_2$H$_5$ |
| 4-CH$_2$CH$_2$OC$_2$H$_5$ | 3-OH-4,5,6-tri-CH$_3$ | 2-CH$_2$SCH$_3$ |
| 2-CH(OCH$_3$)CH$_3$ | 3-OH-6-CH=CH(CH$_3$) | 3-CH$_2$SCH$_3$ |
| 3-CH(OCH$_3$)CH$_3$ | 3-OH-2-CH=CH(CH$_3$) | 2-CH$_2$SOCH$_3$ |
| 4-CH(OCH$_3$)CH$_3$ | 3-OH-4-CH$_2$CH=CH$_2$ | 4-CH$_2$SOCH$_3$ |
| 2-CH(OC$_2$H$_5$)CH$_3$ | 3-OH-2-Cl | 2-CH$_2$SO$_2$CH$_3$ |
| 3-CH(OC$_2$H$_5$)CH$_3$ | 3-OH-5-Cl | 4-CH$_2$SO$_2$CH$_3$ |
| 4-CH(OC$_2$H$_5$)CH$_3$ | 3-OH-6-Cl | 2-CH$_2$SC$_2$H$_5$ |
| 2-(CH$_2$)$_3$OCH$_3$ | 3-OH-2-Br | 3-CH$_2$SC$_2$H$_5$ |
| 3-(CH$_2$)$_3$OCH$_3$ | 2-CH$_2$OCH$_2$CH$_2$OH | 4-CH$_2$SC$_2$H$_5$ |
| 4-(CH$_2$)$_3$OCH$_3$ | 3-CH$_2$O—CH$_2$CH$_2$OH | 2-CH$_2$SOC$_2$H$_5$ |
| 2-C(OCH$_3$)CH$_3$<br>\|<br>CH$_3$ | 4-CH$_2$OCH$_2$CH$_2$OH<br>2-(CH$_2$)$_2$OCH$_2$CH$_2$OH | 3-CH$_2$SOC$_2$H$_5$<br>4-CH$_2$SOC$_2$H$_5$ |
| 3-C(OCH$_3$)CH$_3$<br>\|<br>CH$_3$ | 3-(CH$_2$)$_2$OCH$_2$CH$_2$OH<br>4-(CH$_2$)$_2$OCH$_2$CH$_2$OH | 2-CH$_2$SO$_2$C$_2$H$_5$<br>3-CH$_2$SO$_2$C$_2$H$_5$ |
| 4-C(OCH$_3$)CH$_3$<br>\|<br>CH$_3$ | 2-OH<br>2-OH-3-CH$_3$ | 4-CH$_2$SO$_2$C$_2$H$_5$<br>4-SCH$_2$CH$_2$CH$_3$ |
| 3-OH-2-C$_2$H$_5$ | 2-OH-4-CH$_3$ | 3-SOCH$_2$CH$_2$CH$_3$ |
| 3-OH-4-C$_2$H$_5$ | 2-OH-5-CH$_3$ | 2-SO$_2$CH$_2$CH$_2$CH$_3$ |
| 3-OH-5-C$_2$H$_5$ | 4-OH | 2-SCH(CH$_3$)$_2$ |
| 3-OH-6-C$_2$H$_5$ | 4-OH-2-CH$_3$ | 3-SOCH(CH$_3$)$_2$ |
| 3-OH-2,4-di-CH$_3$ | 4-OH-3-CH$_3$ | 4-SO$_2$CH(CH$_3$)$_2$ |
| 3-OH-2,5-diCH$_3$ | 3-SCH$_3$ | 2-CH$_2$CH$_2$SCH$_3$ |
| 3-OH-4,5-diCH$_3$ | 4-SCH$_3$ | 3-CH$_2$CH$_2$SOCH$_3$ |
| 3-OH-4,6-diCH$_3$ | 2-SOCH$_3$ | 4-CH$_2$CH$_2$SO$_2$CH$_3$ |
| 2-CH$_2$CH$_2$SOC$_2$H$_5$ | 2-CF$_3$ | 6-CH$_2$OCH$_3$-3-Br |
| 3-CH$_2$CH$_2$SO$_2$C$_2$H$_5$ | 3-CF$_3$ | 2-CH$_2$OCH$_3$-3-Cl |
| 4-CH$_2$CH$_2$SC$_2$H$_5$ | 4-CF$_3$ | 4-CH$_2$OCH$_3$-3-Cl |
| 2-SCH$_2$CH$_2$OH | 3-J | 5-CH$_2$OCH$_3$-3-Cl |
| 3-SCH$_2$CH$_2$OH | 2-OCH$_3$-3-Br | 6-CH$_2$OCH$_3$-3-Cl |
| 4-SCH$_2$CH$_2$OH | 4-OCH$_3$-3-Br | 2-CH$_2$OCH$_3$-3-F |
| 2-SOCH$_2$CH$_2$OH | 5-OCH$_3$-3-Br | 4-CH$_2$OCH$_3$-3-F |
| 3-SOCH$_2$CH$_2$OH | 6-OCH$_3$-3-Br | 5-CH$_2$OCH$_3$-3-F |
| 4-SOCH$_2$CH$_2$OH | 2-OCH$_3$-3-Cl | 6-CH$_2$OCH$_3$-3-F |
| 2-SO$_2$CH$_2$CH$_2$OH | 4-OCH$_3$-3-Cl | |
| 3-SO$_2$CH$_2$CH$_2$OH | 5-OCH$_3$-3-Cl | |
| 4-SO$_2$CH$_2$CH$_2$OH | 6-OCH$_3$-3-Cl | |
| 2-SCH$_2$—CH=CH$_2$ | 2-OCH$_3$-3-F | |
| 3-SOCH$_2$CH=CH$_2$ | 4-OCH$_3$-3-F | |
| 4-SO$_2$CH$_2$CH=CH$_2$ | 5-OCH$_3$-3-F | |
| 2-S—CH=CH—CH$_3$ | 6-OCH$_3$-3-F | |
| 3-S—CH=CH—CH$_3$ | 3-F-5-OH | |
| 4-S—CH=CH—CH$_3$ | 3-Cl-5-OH | |
| 4-CH$_2$S—CH$_2$CH=CH$_2$ | 3-Br-5-OH | |
| | 3-J-5-OH | |
| | 2-CH$_2$OH-3-Br | |
| | 4-CH$_2$OH-3-Br | |
| | 5-CH$_2$OH-3-Br | |
| | 6-CH$_2$OH-3-Br | |
| | 2-CH$_2$OH-3-Cl | |
| | 4-CH$_2$OH-3-Cl | |
| | 5-CH$_2$OH-3-Cl | |
| | 6-CH$_2$OH-3-Cl | |
| | 2-CH$_2$OH-3-F | |
| | 4-CH$_2$OH-3-F | |
| | 5-CH$_2$OH-3-F | |
| | 6-CH$_2$OH-3-F | |
| | 5-OC$_2$H$_5$-3-Br | |
| | 5-OC$_2$H$_5$-3-Cl | |
| | 5-OC$_2$H$_5$-3-F | |
| | 2-CH$_2$OCH$_3$-3-Br | |
| | 4-CH$_2$OCH$_3$-3-Br | |
| | 5-CH$_2$OCH$_3$-3-Br | |

TABLE 2

| A' | A' | A' |
|---|---|---|
| [cyclopenta-fused pyridinium with R] | [tetrahydroquinolinium with R] | [cyclopenta-fused isoquinolinium with R] |
| R = H | R = H | R = H |
| = 7-OH | = 8-CH$_3$ | 4-OH |
| = 7-OCH$_3$ | = 8-OH | 4-OCH$_3$ |
| = 7-CH$_2$OH | = 8-OH, 3-CH$_3$ | 1-Cl |
| = 7,7-diCH$_2$OH | = 8-CH$_2$OH | 5-Cl |
| = 7-Cl | = 8-CH$_2$OH, 3-CH$_3$ | |
| = 7-exo-methylene | = 8-OCH$_3$ | |
| = 7-CONH$_2$ | = 8,8-di-CH$_2$OH | |
| = 3-OH | = 8-Cl | |
| = 3-CH$_2$OH | = 8-Br | |

| | | |
|---|---|---|
| | | [tetrahydroisoquinolinium with R] |
| = 4-CH$_3$ | = 8-exo-methylene | R = H |
| = 4-CH$_2$OH | = 8-CONH$_2$ | = 4-OH |
| = 5-OH, 7-CH$_3$ | = 8-Oxo | = 4-OCH$_3$ |
| = 6-OH, 7-CH$_3$ | = 6-Cl | = 1-Cl |
| = 5-CH$_3$ | = 5-OH | = 5-Cl |
| = 6-CH$_3$ | = 5-oxo | |
| = 7-CH$_3$ | = 5-Cl | |
| | = 3-CH$_2$OH | |
| | = 3-OH | |
| | = 4-OCH$_3$ | |

[cyclopentadiene-fused pyridinium]   [benzocyclobutene-fused pyridinium]

[cyclobuta-fused pyridinium]   [dihydroquinolinium]

| [furo-pyridinium] | R = H | [pyrano-pyridinium] | R = H | [thieno-pyridinium] |
|---|---|---|---|---|
| | = 2-CH$_3$ | | = 2-OCH$_3$ | |
| | | | = 3-OH | |

[furo-pyridinium isomer]   [pyrano-pyridinium] = 4-OH   [thieno-pyridinium isomer]

| [furo-pyridinium] | R = H | [pyrano-pyridinium] | [thieno-pyridinium] |
|---|---|---|---|
| | = 3-oxo | | |
| | = 3-OH | | |

[furo-pyridinium]   [pyrano-pyridinium]   [thieno-isoquinolinium]

TABLE 2-continued

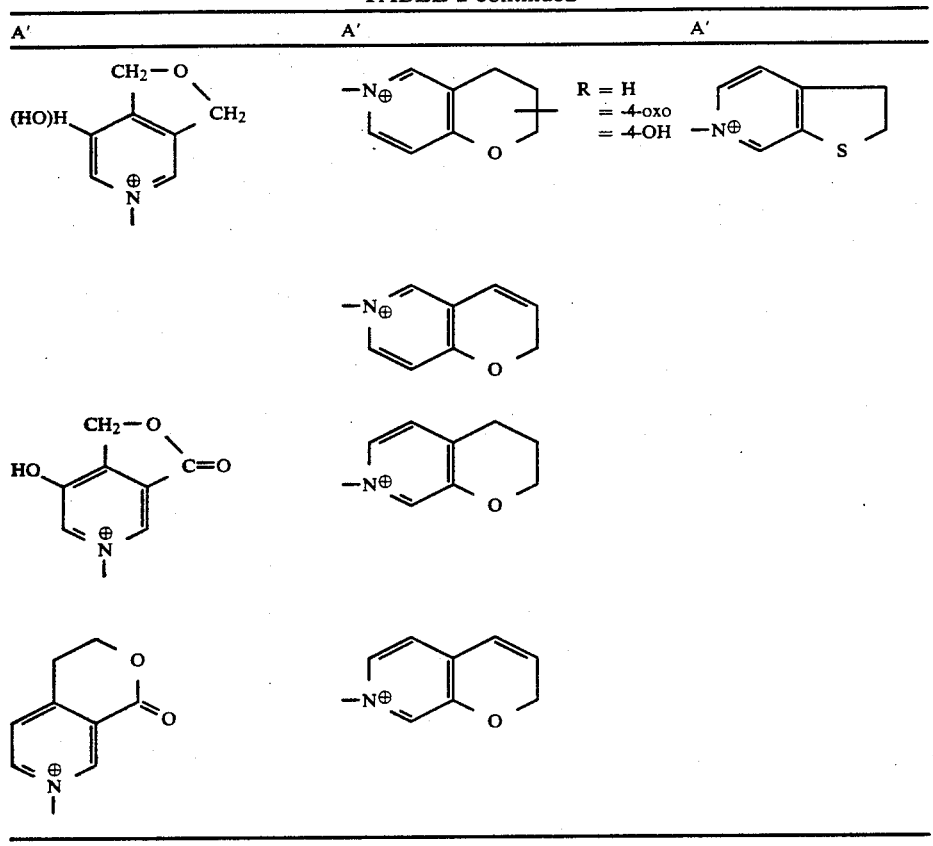

The same compounds as in Tables 1 and 2 are obtained when in the general formula I the radical $R^2$ denotes $C_2H_5$ instead of $CH_3$.

The illustrative examples below of syn compounds which can be prepared according to the invention serve to illustrate the invention in more detail but do not restrict it.

EXAMPLE 1:

7-[2-(2-Aminothiazol-4-yl)-2-syn-methoxyimino-acetamido]3-[(4-ethyl-1-pyridinium)-methyl]-ceph-3-em-4-carboxylate (Process a)

Variant a

A mixture of 6.83 g (15 mmoles) of 7-[2-(2-amino-thiazol-4-yl)-2-syn-methoxyimino-acetamido]-cephalosporanic acid, 1.38 g (16.5 mmoles) of sodium bicarbonate, 74.7 g (450 mmoles) of potassium iodide, 16.07 g (150 mmoles) of 4-ethylpyridine and 70 ml of water was stirred for 5 hours at 50°–55° C. During this period the pH was maintained at a value between 6.8 and 7.2 by the occasional addition of sodium bicarbonate. The mixture was diluted with 500 ml of acetone and chromatographed over silica gel (Merck 0.063–0.2 mm, 25×3 cm column). Potassium iodide is eluted with acetone/water (7:1) and thereafter the title compound is eluted with acetone/water (3:1). The freeze-dried crude product was rechromatographed over silica gel (Merck "Lobar" column C, about 1 bar, acetone/water 3:1). Freeze-drying of the product fractions produced 3.7 g of the title compound in the form of a colorless solid.

$^1$H-NMR (CF$_3$CO$_2$D): $\delta=1.46$ (t, J=7 Hz, 3H, CH$_2$—CH$_3$); 3.07 (q, J=7 Hz, 2H, CH$_2$—CH$_3$); 3.50 and 3.77 (AB, J=19 Hz, 2H, S-CH$_2$); 4.23 (s, 3H, OCH$_3$); 5.19–6.22 (m, 4H, CH$_2$Py and 2 lactam-H); 7.37 (s, 1H, thiazole); 7.91 and 8.80 ppm (AA'BB', J=6 Hz, 4H, Py).

IR (KBr): 1,775 cm$^{-1}$ (lactam-CO).

Variant b

The title compound was obtained in the same purity as above and in a yield of 4.9 when 6.83 g (15 mmoles) of 7-[2-(2-(aminothiazol-4-yl)-2-syn-methoxyimino-acetamido]-cephalosporanic acid, 1.38 g (16.5 mmoles) of sodium bicarbonate, 4.8 g (45 mmoles) of 4-ethylpyridine, 31.5 g (210 mmoles) of sodium iodide and 21 ml of water were stirred for 110 hours at 25° C.

Variant c

Using the amounts of the components as described under variant b and a reaction time of 1 hour at 80° C., produced 4.5 g of the title compound in the form of a colorless solid.

Procedures analogous to Example 1 produced the compounds which are listed below, corresponding to the general formula I in which $R^1$ denotes hydrogen and $R^2$ denotes methyl, and carry, in the pyridinium radical (A in the formula I), the substitutents indicated in the second column of Table 3.

The numeral attached to the substituents indicates in each case the precise position of the substituent(s) in the pyridinium radical.

TABLE 3

| Example | Substituent | Yield % of theory | Comments | $^1$H-NMR: δ(ppm) |
|---|---|---|---|---|
| 2 | 3-C$_2$H$_5$ | 61 | Rechromatographed with acetone/water 2:1 | (F$_3$CCO$_2$D): 1.57(t, J=7Hz, 3H, CH$_2$—CH$_3$); 3.00(q, J=7Hz, 2H, CH$_2$—CH$_3$); 3.49 and 3.27 (AB, J=20Hz, 2H, S—CH$_2$); 4.22(s, 3H, OCH$_3$); 5.24–6.28(m, 4H, CH$_2$—Py and 2 lactam-H); 7.35(s, 1H, thiazole); 7.86-8.77 (m, 4H, Py) |
| 3 | 2-C$_2$H$_5$ | 28 | Rechromatographed with acetone/water 2:1 | (F$_3$CCO$_2$D): 1.57(t, J=7Hz, 3H, CH$_2$—CH$_3$); 3.12-3.99(m, 4H, CH$_2$—CH$_3$ and S—CH$_2$); 4.23(s, 3H, OCH$_3$); 5.35-6.12(m, 4H, CH$_2$—Py and 2 lactam-H); 7.36(s, 1H, thiazole), 7.80-8.76 (m, 4H, Py) |
| 4 | 4-CH$_2$CH$_2$CH$_3$ | 45 | Rechromatographed with acetone/water 2:1 | (F$_3$CCO$_2$D): 1.09(t, J=7Hz, 3H, CH$_2$—CH$_3$); 1.85(sx, J=7Hz, 2H, CH$_2$—CH$_2$—CH$_3$); 2.87-4.06(m, 4H, CH$_2$—CH$_2$ and S—CH$_2$); 4.22 (s, 3H, OCH$_3$); 5.17-6.21(m, 4H, CH$_2$Py and 2 lactam H); 7.35 (s, 1H, thiazole); 7.86 and 8.78 (AA'BB', J=6Hz, 4H, Py) |
| 5 | 4-iso-C$_3$H$_7$ | 47 | Rechromatographed with acetone/water 4:1 | (F$_3$CCO$_2$D): 1.46(d, J=7Hz, 6H, iso-C$_3$H$_7$); 2.97-4.07(m, 3H, iso-C$_3$H$_7$ and S—CH$_2$); 4.23(s, 3H, OCH$_3$); 5.17-6.23(m, 4H, CH$_2$—Py and 2 lactam-H); 7.37(s, 1H, thiazole); 7.93 and 8.82 (AA'BB', J=6Hz, 4H, Py) |
| 6 | 2-CH$_3$ | 37 | Rechromatography with acetone/water (2:1) produced small amounts of the Δ2-isomer as a by-product. | (F$_3$CCO$_2$D): 2.98(s, 3H PyCH$_3$); 3.52 and 3.71(AB, J=19Hz, 2H, S—CH$_2$); 4.24(s, 3H, OCH$_3$); 5.35-6.12(m, 4H, CH$_2$Py and 2 lactam-H); 7.37(s, 1H, thiazole); 7.79-8.76 (m, 4H, Py) |
| 7 | 4-t-C$_4$H$_9$ | 41 | Rechromatographed with actone/water 2:1 | (F$_3$CCO$_2$D): 1.51(t, 9H, C$_4$H$_9$); 3,48 and 3.79(AB, J=19Hz, 2H, S—CH$_2$); 4.23(s, 3H, OCH$_3$), 5.16-6.21(m, 4H, CH$_2$—Py and 2-lactam-H); 7.36(s, 1H, thiazole); 8.07 and 8.82(AA'BB', J=7Hz, 4H, Py) |
| 8 | 3-CH$_3$-4-CH$_3$ | 47 | Rechromatographed with acetone/water 2:1 | (F$_3$CCO$_2$D): 2.55(s, 3H, CH$_3$Py); 2.66(s, 3H, CH$_3$Py); 3.47 and 3.74 (AB, J=19Hz, 2H, S—CH$_2$); 4.22(s, 3H, OCH$_3$); 5.11-6.21(m, 4H, CH$_2$—Py and 2 lactam-H); 7.35 (s, 1H, thiazole); 7.76-8.61(m, 3H, Py) |
| 9 | 3-CH$_3$-5-CH$_3$ | 51 |  | (F$_3$CCO$_2$D): 2.62(s, 6H, CH$_3$Py); 3.47 and 3.74(AB, J=19Hz, 2H, S—CH$_2$); 4.22(s, 3H, OCH$_3$) 5.14-6.27(m, 4H, CH$_2$—Py and 2 lactam-H); 7.36(s, 1H, thiazole); 8.18-8.57(m, 3H, Py) |
| 10 | 3-C$_2$H$_5$-4-CH$_3$ | 38 | Rechromatographed with acetone/water 4:1 | (F$_3$CCO$_2$D): 1.40(t, J=7Hz, 3H, CH$_2$—CH$_3$); 2.69(s, 3H, PyCH$_3$); 2.94(q, J=7Hz, 2H, CH$_2$—CH$_3$); 3.47 and 3.73(AB, J=19Hz, 2H, S—CH$_2$); 4.20(s, 3H, OCH$_3$); 5.14-6.21(m, 4H, CH$_2$—Py and 2 lactam-H); 7.34(s, 1H, thiazole); 7.74-7.86(m, 1H, Py); 8.49-8.70 (m, 2H, Py) |
| 11 | 3-C$_2$H$_5$-6-CH$_3$ | 22 | Rechromatographed with acetone/water 4:1 | (F$_3$CCO$_2$D): 1.39(t, J=7Hz, 3H, CH$_2$—CH$_3$); 2.73-3.11(m, 5H, CH$_2$—CH$_3$ and PyCH$_3$); 3.44 and 3.61(AB, J=19Hz, 2H, S—CH$_2$; 4.23(s, 3H, OCH$_3$); 5.33-6.09(m, 4H, CH$_2$—Py and 2 lactam-H); 7.35(s, 1H, thiazole); 7.77-8.51 (m, 3H, Py) |
| 12 | 2-CH$_2$C$_6$H$_5$ | 11 | Rechromatographed with acetone/water 4:1 | (F$_3$CCO$_2$D): 3.17 and 3.33(AB, J=19Hz, 2H, S—CH$_2$); 4.23(s, 3H, OCH$_3$); 4.61(s, 2H, CH$_2$C$_6$H$_5$); 5.22-6.07(m, 4H, CH$_2$—Py and 2 Lactam-H); 7.03-7.77(m, 6H, |

TABLE 3-continued

| Example | Substituent | Yield % of theory | Comments | $^1$H-NMR: δ(ppm) |
|---|---|---|---|---|
| | | | | thiazole and $C_6H_5$); 7.77–8.83 (m, 4H, Py) |
| 13 | 4-$C_6H_5$ | 12 | Rechromatographed with acetone/water 4:1 | ($F_3CCO_2D$): 3.55 and 3.82(AB, J=19Hz, 2H, S—$CH_2$); 4.20(s, 3H, $OCH_3$); 5.20–6.26(m, 4H, $CH_2$—Py and 2 lactam-H); 7.35(s, 1H, thiazole) 7.51–7.89(m, 5H, $C_6H_5$); 8.26 and 8.91(AA'BB', J=7Hz, 4H, Py) |
| 14 | 2-$CH_2OH$ | 38 | | ($CF_3CCO_2D$): 3.55 and 3.76(AB, J=18Hz, 2H, S—$CH_2$); 4.23(s, 3H, $OCH_3$); 5.32–6.20(m, 6H, $CH_2$—Py, $CH_2OH$, 2 lactam-H); 7.38(s, 1H, thiazole); 7.90–8.89(m, 4H, Py) |
| 15 | 3-$CH_2OH$ | 58 | Reaction time: 8 days at 25° C. | ($CF_3COOD$): 3.54 and 3.79 (AB, J=18Hz, 2H, S—$CH_2$); 4.22(s, 3H, $OCH_3$), 5.17(s, 2H, $CH_2OH$), 5.14–6.32(m, 4H, $CH_2$Py+2 lactam-H); 7,38(s, 1H, thiazole); 7.95–9.10 (m, 4H, Py) |
| 16 | 3-OH | 47 | Rechromatographed over XAD-2 with water | ($D_2O$): 3.21 and 3.45(AB, J=17Hz, 2H, $CH_2S$); 3.93(s, 3H, $OCH_3$); 5.35–5.85(m, 4H, $CH_2$—Py and 2 lactam-H); 6.93(s, 1H, thiazole); 7.43–7.95(m, 4H, Py) |
| 17 | 2-CHCH$_3$<br>\|<br>OH | 35 | Reaction time: 110 hours at 23° C. + 2 hours at 50° C. | ($F_3CCO_2D$): 1.76(d, J=7Hz, CH—$CH_3$); 3.20–4.36(m, 3H, $SCH_2$ and $CH$—$CH_3$) 4.22(s, 3H, $OCH_3$); 5.23–6.30(m, 4H, $CH_2$—Py and 2 lactam-H) 7.36 (s, 1H, thiazole); 7.98–9.31(m, 4H, Py) |
| 18 | 3-CH—$CH_3$<br>\|<br>OH | 67 | Reaction time: 110 hours at 23° C. + 2 hours at 50° C. Obtained pure after 1st chromatography. | ($F_3CCO_2D$): 1.88(d, J=6Hz, CH—$CH_3$); 3.23–4.43(m, 3H, $SCH_2$ and $CH$—$CH_3$); 4.22(s, 3H, $OCH_3$); 5.38–6.39(m, 3H, $CH_2$—Py and 2 lactam-H); 7.37 (s, 1H, thiazole); 7.90–8.88(m, 4H, Py) |
| 19 | 4-CH($CH_3$)OH | 64 | Rechromatographed with acetone/water 4:1 | ($F_3CCO_2D$): 1.75(d, J=7Hz, CH—$CH_3$); 3.23–4.38(m, 6H, S—$CH_2$, $OCH_3$ and $CH$—$CH_3$); 5.24–6.30(m, 4H, $CH_2$—Py and 2 lactam-H); 7.37(s, 1H, thiazole); 8.16 and 8.94(AA',BB', J=6Hz, 4H, Py) |
| 20 | 3-C($CH_3$)$_2$OH | 58 | Rechromatographed with acetone/water 4:1 | ($F_3CCO_2D$): 1.83(s, 6H, $CH_3$); 3.54 and 3.78(AB, J=20Hz, 2H, S—$CH_2$); 4.21(s, 3H, $OCH_3$); 5.33–6.28(m, 4H, $CH_2$—Py and 2 lactam-H; 7.36(s, 1H, thiazole) 7.96–9.26(m, 4H, Py) |
| 21 | 4-C($CH_3$)$_2$OH | 56 | Rechromatographed with acetone/water 4:1 | ($F_3CCO_2D$): 1.83(s, 6H, $CH_3$); 3.51 and 3.81(AB, J=19Hz, 2H, S—$CH_2$); 4.23(s, 3H, $OCH_3$); 5.23–6.24(m, 4H, $CH_2$—Py and 2 lactam-H); 7.36(s, 1H, thiazole); 8.21 and 8.92(AA'BB', J=7Hz, 4H, Py) |
| 22 | 3-$CH_2CH_2CH_2OH$ | 38 | Rechromatographed with acetone/$H_2O$ 4:1, reaction time 3 days at 23° C. + 2 hours at 50° C. | ($F_3CCO_2D$): 2.17(m, 2H, propyl), 2.90–4.25(m, 6H, S—$CH_2$ and 4 propyl-H) 4.22(s, 3H, $OCH_3$); 5.20–6.88(m, 4H, $CH_2$Py and 2 lactam-H); 7.36(s, 1H, thiazole); 7.90–8.86(m, 4H, Py) |
| 23 | 3-$COCH_3$ | 47 | Rechromatographed over XAD-2 (column 10 × 2 cm) with methanol/water 4:1 | ($F_3CCO_2D$): 2.91(s, 3H, Ac); 3.61 and 3.86(AB, J=19Hz, 2H, S—$CH_2$); 4.24(s, 3H, $OCH_3$), 5.34–6.39(m, 4H, $CH_2$Py and 2 lactam-H), 7.36 (s, 1H, thiazole, 8.17–9.60(m, 4H, Py) |
| 24 | 3-$COC_6H_5$ | 18 | | ($F_3CCO_2D$): 3.64 and 3.87(AB, J=19Hz, 2H, S—$CH_2$); 4.23(s, 3H, $OCH_3$); 5.35–6.42(m, 4H, $CH_2$Py and 2 lactam-H); 7.37–9.45(m, 10H, thiazole, ($C_6H_5$ and Py) |
| 25 | 4-$COC_6H_5$ | 21 | Rechromatographed over XAD-2 with methanol/ water 4:1 | ($F_3CCO_2D$): 3.62 and 3.87(AB, J=19Hz, 2H, S—$CH_2$); 4.23(s, 3H, $OCH_3$); 5.35–6.41(m, 4H, $CH_2$—Py and 2 lactam-H); 7.37–9.26(m, 10H, thiazole, $C_6H_5$ and Py) |

TABLE 3-continued

| Example | Substituent | Yield % of theory | Comments | $^1$H-NMR: δ(ppm) |
|---|---|---|---|---|
| 26 | 4-OCH$_3$ | 45 | | (CF$_3$COOD): 3.48 and 3.72(AB, J=18Hz, 2H, S—CH$_2$); 4.20(s, 3H, OCH$_3$); 4.23(s, 3H, OCH$_3$); 5.03–6.10(m, 4H, CH$_2$—Py and 2 lactam-H); 7.36–7.48(3H, thiazole-H, 2 Py—H); 8.62–8.75(AA'BB', J=7Hz, 2H, Py) |
| 27 | 4-CH$_2$OCH$_3$ | 57 | Rechromatographed over XAD-2 with water | (CF$_3$COOD): 3.25–4.05(AB, J=18Hz, 2H, SCH$_2$); 3.71(s, 3H, CH$_2$OCH$_3$); 4.22(s, 3H, OCH$_3$); 4.95(s, 2H, CH$_2$OCH$_3$); 5.23–6.28(m, 4H, CH$_2$—Py and 2 lactam-H); 7.35(q, 1H, thiazole); 8.10 and 8.95(AA'BB', J=6Hz, 4H, Py) |
| 28 | 2-SCH$_3$ | 14 | | (CF$_3$COOD): 2.91(s, 3H SCH$_3$); 3.52 and 3.74(AB, J=18Hz, 2H, S—CH$_2$); 4.24(s, 3H, OCH$_3$); 5.25–6.55(m, 4H, CH$_2$Py - 2lactam-H); 7.36(s, 1H, thiazole); 7.55–8.80(m, 4H, Py) |
| 29 | 4-CH$_2$S—CH$_3$ | 25 | | (CF$_3$COOD): 2.14(s, 3H, CH$_3$); 3.47 and 3.80(AB, J=18Hz, 2H, S—CH$_2$); 3.94(s, 2H, CH$_2$S); 4.20 (s, 3H, OCH$_3$); 5.18–6.20(m, 4H, CH$_2$—Py and 2 lactam-H); 7.35 (s, 1H, thiazole); 8.15 and 8.85 (AA'BB', J=6Hz, 4H, Py) |
| 30 | 3-CH$_2$SOCH$_3$ | 12 | Rechromatographed with acetone/water 4:1 | (CF$_3$COOD): 3.01(s, 3H, SOCH$_3$); 3.60 and 3.81(AB, 2H, SCH$_2$); 4.24(s, 3H, OCH$_3$); 4.57(s, 2H, CH$_2$SO); 5.25–6.58(m, 4H, CH$_2$—Py and 2 lactam-H); 7.34(s, 1H, thiazole); 8.05–9.10(m, 4H, Py) |
| 31 | 3-CH$_2$SO$_2$CH$_3$ | 23 | | (CF$_3$COOD); 3.34(s, 3H, SO$_2$CH$_3$); 3.62 and 3.82(AB, 2H, S—CH$_2$); 4.23(s, 3H, OCH$_3$); 4.88(s, 2H, CH$_2$SO$_2$); 5.30–6.35(m, 4H, CH$_2$—Py and 2 lactam-H); 7.35(s, 1H, thiazole); 8.05–9.18(m, 4H, Py) |
| 32 | 3-F | 45 | Rechromatographed with methanol/water 4:1 | (D$_6$-DMSO): 3.76(s, 3H, OCH$_3$); 4.52–5.96(m, 4H, CH$_2$—Py and 2 lactam-H); 6.63(s, 1H, thiazole); 7.10 (bs, 2H, NH$_2$); 7.80–9.86(m, 5H, Py and NH) |
| 33 | 4-NHCOCH$_3$ | 22 | | (CF$_3$COOD): 2.46(s, 3H, COCH$_3$); 3.47 and 3.80(AB, J=18Hz, 2H, S—CH$_2$); 4,21(s, 3H, OCH$_3$); 5.12–6.35(m, 4H CH$_2$—Py and 2 lactam-H); 7.35(s, 1H thiazole); 8.26 and 8.73 (AA'BB', J=6Hz, 4H, Py) |
| 34 | 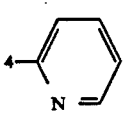 | 28 | Variant b, 20% of acetone added to the reaction meduim | (CF$_3$COOD): 3.60 and 3.87(AB, J=18Hz, 2H, S—CH$_2$); 4.20(s, 3H, OCH$_3$); 5.28–6.38(AB, 3H, CH$_2$—Py); 5.37(d, J=5Hz, C$_6$-lactam-H); 6.08 (d, J=5Hz, C$_7$-lactam-H); 7.38(s, 1H, thiazole); 8.15–9.41(m, 8H, Py) |
| 35 | 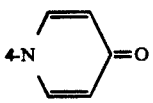 | 57 | Rechromatographed with acetone/water 2:1 | (D$_2$O): 3.33 and 3.63(AB, J=18Hz, 2H, S—CH$_2$); 3.86(s, 3H, OCH$_3$); 5.05–5.76(m, 4H, CH$_2$—Py and 2 lactam-H); 6.76(s, 1H, thiazole); 6,53–6,80; 8.08–8.38; 9.00–9.15 (8H, Py) |
| 36 | 3-CO$_2$C$_2$H$_5$ | 27 | Rechromatographed over XAD-2 with water | (F$_3$CCO$_2$D): 1.54(t, J=7Hz, 3H, CH$_2$—CH$_3$); 3.33–4.14(AB, 2H, S—CH$_2$); 4.23(s, 3H, OCH$_3$); 4.66(q, J=7Hz, 2H, CH$_2$CH$_3$); 5.35–6.36(m, 4H, CH$_2$—Py and 2 lactam-H); 7.37(s, 1H, thiazole); 8.13–9.67(m, 4H, Py) |
| 37 | 4-CO$_2$C$_2$H$_5$ | 48 | | (D$_6$-DMSO): 1.35(t, J=7Hz, 3H, CH$_2$CH$_3$); 3.77(s, 3H, OCH$_3$); 4.22–5.62(m, 6H, CH$_2$CH$_3$, CH$_2$Py and 2 lactam-H); 6.62(s, 1H, thiazole); 7.08(bs, 2H, H$_2$N-thiazole); 8.44(AA'BB', J=6Hz, 2H, Py); 9.33–9.63(m, 5H, Py and amide) |

TABLE 3-continued

| Example | Substituent | Yield % of theory | Comments | $^1$H-NMR: δ(ppm) |
|---|---|---|---|---|
| 38 | 3-CH$_2$—CO$_2$H | 19 | Rechromatographed with acetone/water 4:1 | (F$_3$CCO$_2$D); 3.55 and 3.81(AB, J=19Hz, 2H, S—CH$_2$); 4.17(s, 2H, CH$_2$CO$_2$H); 4.22(s, 3H, OCH$_3$); 5.28–6.36(m, 4H, CH$_2$—Py and 2 lactam-H); 7.36(s, 1H, thiazole); 7.97–9.04(m, 4H, Py); |
| 39 | 3-CH$_2$CO$_2$C$_2$H$_5$ | 47 | Rechromatographed with acetone/water 4:1 | (F$_3$CCO$_2$D): 1.39(t, J=7Hz, CH$_2$CH$_3$); 3.29–4.55(m, 9H, S—CH$_2$, Py—CH$_2$, CH$_2$—CH$_3$ and OCH$_3$); 5.29–6.33(m, 4H, CH$_2$—Py and 2 lactam-H); 7.36(s, 1H, thiazole); 7.95–9.02(m, 4H, Py) |
| 40 | 4-CONHCONHC$_2$H$_5$ | 28 | Rechromatographed with acetone/water 4:1 | (CF$_3$COOD): 1.43(t, 3H, CH$_2$CH$_3$); 3.25–4.23(m, 4H, SCH$_2$ and CH$_2$ CH$_3$); 4.22(s, 3H, OCH$_3$); 5.12–6.35(m, 4H, CH$_2$Py+2 lactam-H); 7.37(s, 1H, thiazole); 8.62 and 9.24(AA'BB', J=6Hz, 4H, Py) |
| 41 | 4-CH$_2$CONH$_2$ | 43 | | (D$_2$O): 3.23 and 3.53(AB, J=18Hz, 2H, S—CH$_2$); 3.93(s, 3H, OCH$_3$); 5.22(d, 1H, J=5Hz, C$_6$-lactam-H); 5.31 and 5.44(AB, 2H, CH$_2$—Py); 5.81(d, 1H, J=5Hz, C$_7$-lactam-H); 6.92(s, 1H, thiazole); 7.93 and 8.80(AA'BB', J=6Hz, 4H, Py) |
| 42 | 3-CONH$_2$ | 47 | | (CF$_3$COOD): 3.60 and 3.83(AB, J=18Hz, 2H, SCH$_2$); 4.22(s, 3H, OCH$_3$); 5.33–6.38(m, 4H, CH$_2$—Py and 2 lactam-H); 7.36(s, 1H, thiazole); 8.12–9.60(m, 4H, Py) |
| 43 | 3-CONHCO$_2$C$_2$H$_5$ | 17 | | (CF$_3$COOD): 1.40(t, J=7Hz, 3H, CH$_2$CH$_3$); 3.25–4.26(m, 4H, S—CH$_2$, CH$_2$—CH$_3$); 4.25(s, 3H, OCH$_3$); 5.28–6.40(4H, CH$_2$—Py and 2 lactam-H); 7.38(s, 1H, thiazole); 8.08–9.62(m, 4H, Py) |
| 44 | 4-CONHCO$_2$C$_2$H$_5$ | 19 | | (CF$_3$COOD): 1.45(t, J=7Hz, 3H, CH$_2$CH$_3$); 3.25–4.61(m, 4H, SCH$_2$ and CH$_2$CH$_3$); 4.23(s, 3H, OCH$_3$); 5.25–6.40(m, 4H, 2 lactam-H and CH$_2$—Py) 7.36(s, 1H, thiazole); 8.42–9.30 (m, 4H, Py) |
| 45 | 4-CONHC$_2$H$_5$ | 43 | | (CF$_3$COOD): 1.38(t, J=7Hz, 3H, CH$_2$CH$_3$); 3.15–4.25(m, 4H, S—CH$_2$, CH$_2$—CH$_3$); 4.23(s, 3H, OCH$_3$); 5.28–6.33(4H, CH$_2$—Py and 2-lactam-H); 7.36(s, 1H, thiazole); 8.41–9.20(AA'BB', J=7Hz, 4H, Py) |
| 46 | 3-CON(C$_2$H$_5$)$_2$ | 36 | | (CF$_3$COOD): 1.22–1.53(m, 6H, C$_2$H$_5$); 3.15–4.25(m, 6H, S—CH$_2$ and C$_2$H$_5$); 4.25(s, 3H, OCH$_3$); 5.35–6.40 (m, 4H, CH$_2$—Py and 2-lactam-H); 7.41(s, 1H, thiazole); 8.10–9.22(m, 4H, Py) |
| 47 | 4-CN | 31 | | (D$_2$O): 3.22 and 3.42(AB, J=17Hz, 2H, SCH$_2$); 3.93(s, 3H, OCH$_3$); 5.15–5.92(m, 4H, CH$_2$—Py and 2 lactam-H); 6.93(s, 1H, thiazole) 8.25–9.28(AA'BB', 4H, Py) |
| 48 | 4-SO$_2$NH$_2$ | 26 | Rechromatographed over XAD-2 with water | (CF$_3$COOD): 3.55 and 3.82(AB, J=19Hz, 2H, SCH$_2$); 4.23(s, 3H, OCH$_3$); 5.30–6.33(m, 4H, CH$_2$—Py and 2 lactam-H); 7.40(s, 1H, thiazole); 8.65 and 9.15(AA'BB', J=7Hz, 4H, Py) |
| 49 | 4-CH$_2$CH$_2$SO$_3$K | 42 | Rechromatographed over HP 20 adsorption resin, Mitsubishi Co. | (D$_6$-DMSO): 2.30–4.05(m, 6H, S—CH$_2$ and CH$_2$—CH$_2$); 3.75(s, 3H, OCH$_3$); 4.75–5.72(m, 4H, CH$_2$—Py and 2 lactam-H); 6.63(s, 1H, thiazole) 7.12(bs, 2H, NH$_2$); 7.96 and 9.25 (AA'BB', J=7Hz, 4H, Py); 9.45(d, J=8Hz, NH) |

A procedure analogous to Example 1, variant b, produced the compounds which are listed below, correspond to the general formula I in which R$^1$ denotes hydrogen and $R^2$ denotes methyl, and carry the substituent indicated in the second column of Table 4 as the radical A.

EXAMPLE 54

7-[2-(2-Aminothiazol-4-yl)-2-syn-ethoxyimino-

TABLE 4

| Example | A | Yield % of theory | Comments | $^1$H-NMR: δ (ppm) |
|---|---|---|---|---|
| 50 | (cyclopentene-fused pyridinium) | 48 | Rechromatographed with acetone/water 4:1 Reaction time: 3 days at 23° C. and 2 hours at 50° C. with 30% of acetone added to the reaction medium | ($CF_3COOD$): 2.40–2.70(m, 2H, cyclopentene-H); 3.22–4.23 (m, 6H, 4-cyclopentene-H and S—$CH_2$); 4.23(s, 3H, $OCH_3$); 5.28–6.36 (m, 4H, $CH_2$—Py and 2 lactam-H); 7.37(s, 1H, thiazole); 7.66–8.58(m, 4H, Py) |
| 51 | (cyclohexene-fused pyridinium) | 38 | Rechromatographed with acetone/water 4:1 Reaction time: 3 days at 23° C. and 2 hours at 50° C. with 30% of acetone added to the reaction medium | ($CF_3COOD$): 2.10(m, 4H, cyclohexene-H); 3.18(m, 4H, cyclohexene-H); 3.50 and 3.70(AB, J=19Hz, 2H, S—$CH_2$); 4.25(s, 3H, $OCH_3$); 5.38(d, J=5Hz, $C_6$-lactam-H); 5.55 and 3.80(AB, 2H, $CH_2$—Py); 6.08(d, J=5Hz, $C_7$-lactam-H); 7.39(s, 1H, thiazole); 7.65–8.58(m, 3H, Py) |

EXAMPLE 52

7-[2-(2-Aminothiazol-4-yl)-2-syn-ethoxyimino-acetamido]-3-(1-pyridiniummethyl)-ceph-3-em-3-carboxylate A mixture of 7.25 g (15 mmoles) of 7-[2-(2-aminothiazol-4-yl)-2-syn-ethoxyimino-acetamido]-cephalosporanic acid, 1.38 g (16.5 mmoles) of sodium bicarbonate, 41.5 g (250 mmoles) of potassium iodide, 5.92 g (75 mmoles) of pyridine and 20 ml of water was stirred for 5 hours at 60° C. The residue obtained after freeze-drying was taken up in a little acetone/water and chromatographed over silica gel (Merck 0.063–0.2 mm, 40×4 cm column). Potassium iodide was eluted with acetone/water (20:1) and thereafter the title compound was eluted with acetone/water (4:1). The crude product was chromatographed over silica gel (Merck "Lobar" column, about 1 bar, acetone/water 4:1). Freeze-drying the product fractions produced 3.4 g of the title compound in the form of a colorless solid.

$^1$H-NMR ($D_6$-DMSO): δ=1.21 (t,J=7 Hz,3H,$CH_2$—$\underline{CH_3}$); 4.08 (q,J=7 Hz,2H,$\underline{CH_2}$—$CH_3$); 4.85–5.73 (m,4H,$CH_2$Py and 2 lactam-H); 6.65 (s,1H, thiazole), 7.12 (bs,2H,$H_2$N-thiazole); 8.08–9.47 ppm (m, 6H,Py and amide).

IR (KBr): 1775 $cm^{-1}$ (lactam-CO).

The following compounds were prepared analogously to Example 52.

EXAMPLE 53

7-[2-(2-Aminothiazol-4-yl)-2-syn-ethoxyimino-acetamido]-3-[(3-methyl-1-pyridinium)-methyl]-ceph-3-em-4-carboxylate Colorless solid, yield 47% of theory.
$^1$H-NMR ($D_6$-DMSO): δ=1.19 (t,J=7 Hz,3H,$CH_2$—$\underline{CH_3}$); 2.48 (m,DMSO and Py-$CH_3$); 3.29 (bs,$H_2O$+S—$CH_2$); 4.08 (q,J=7 Hz,2H,$\underline{CH_2}$—$CH_3$); 4.85–5.71 (m,4H,$CH_2$Py and 2 lactam-H); 6.63 (s,1H, thiazole); 7.08 (bs,2H,$H_2$N-thiazole); 7.85–9.46 ppm (m,5H,Py and amide).

acetamido]-3-[(4-hydroxymethyl-1-pyridinium)-methyl]-ceph-3-em-4-carboxylate

Colorless solid, yield 52% of theory.
$^1$H-NMR ($D_6$-DMSO): δ=1.21 (t,J=7 Hz,3H,$CH_2$—$CH_3$); 3.31 (bs,$H_2O$+S—$CH_2$); 4.10–5.72 (m,9H,$CH_2CH_3$,$CH_2OH$, $CH_2$Py and 2 lactam-H); 6.63 (s,1H,thiazole); 6.9–7.3 (m, 3H,$H_2$N and 1 Py-H); 7.92–9.45 (m,4H,3Py-H and amide).

EXAMPLE 55

7-[2-(2-Amino-5-chlorothiazol-4-yl)-2-syn-methoxyimino-acetamido]-3-[(2-methyl-1-pyridinium)-methyl]-ceph-3-em-4-carboxylate A mixture of 0.98 g (2 mmoles) of 7-[2-(2-amino-5-chlorothiazol-4-yl)-2-syn-methoxyimino-acetamido]-cephalosporanic acid, 0.18 g (2.2 mmoles) of sodium bicarbonate, 6.6 g (40 mmoles) of potassium iodide, 1.8 g (20 mmoles) of 2-picoline and 8 ml of water was stirred for 5 hours at 60° C. During this period the pH was maintained at a value between 6.5 and 7 by the occasional addition of sodium bicarbonate. The mixture was diluted with 70 ml of acetone and chromatographed over silica gel (Merck 0.063–0.2 mm, column 10×2 cm). Potassium iodide was eluted with acetone/water (7:1) and thereafter the title compound was eluted with acetone/water (3:1). The crude product (0.2 g) was rechromatographed over silica gel (Merck "Lobar" column B, about 1 bar, acetone/water 3:1). Freeze-drying the product fractions produced 0.13 g of the desired compound in the form of a colorless solid and small amounts of the Δ2-isomer.

$^1$H-NMR ($CF_3 CO_2D$): δ=2.98 (s,3H,Py-$CH_3$); 3.51 and 3.74 (AB,J=19 Hz, 2H,S—$CH_2$); 4.20 (s,3H,$OCH_3$); 5.34–6.11 (m,4H,$CH_2$-Py and 2 lactam-H); 7.77–8.73 ppm (m,4H,Py).

IR (KBr): 1770 $cm^{-1}$ (lactam-CO).

The following compound was prepared analogously to Example 55.

EXAMPLE 56

7-[2-(2-Amino-5-chlorothiazol-4-yl)-2-syn-methoxyiminoacetamido]-3-[(4-methyl-1-pyridinium)-methyl]-ceph-3-em-4-carboxylate $^1$H-NMR: (CF$_3$ CO$_2$D): δ=2.75 (s,3H,Py-CH$_3$); 3.49 and 3.77 (AB,J=19 Hz, 2H,S—CH$_2$); 4.19 (s,3H,OCH$_3$); 5.16–6.20 (m,4H,CH$_2$-Py and 2 lactam-H); 7.86 and 8.76 ppm (AA'BB', J=6 Hz,4H,Py).

Comment: Rechromatography produced small amounts of the Δ2-isomer.

EXAMPLE 57

7-[2-(2-Aminothiazol-4-yl)-2-syn-methoxyiminoacetamido]-3-[(4-ethyl-1-pyridinium)-methyl]-ceph-3-em-4-carboxylate Process b)

a) 7-tert.-Butoxycarbonylaminocephalosporanic acid

A mixture of 12.8 g (50 mmoles) of 7-aminocephalosporanic acid, 20.3 g (0.1 mole) of bis-trimethylsilyl acetamide, 22 g (0.1 mole) of di-tert.-butyl dicarbonate and 150 ml of methylene chloride was left for 10 days at room temperature. The solution was then stirred for 3 hours after the addition of 200 ml of ice water. Unconverted 7-aminocephalosporanic acid was filtered off with suction, the organic phase of the filtrate was separated off, and the aqueous phase was extracted twice more with methylene chloride. The organic phase was washed several times with water and dried with magnesium sulfate. After the solvent had evaporated, 11 g (59% of theory) of an amorphous yellowish product remained.

NMR (D$_6$-DMSO): δ=1.41 (s,9H,tert-butyl); 2.00 (s,3H,acetyl); 2.8–3.61 3.6 (2H,SCH$_2$+H$_2$O); 4.5–5.07 (m,3H,C$_6$-lactam-H) and CH$_2$OAc); 5.41 (dd,J=4.5 and 9 Hz,C$_7$-lactam-H); 7.9 ppm (d,J=9 Hz;NH).

IR (KBr): 1785 (lactam-CO), 1725 cm$^{-1}$ (ester).

b) 7-tert.-Butoxycarbonylamino-3-[(4-ethyl-1-pyridinium)-methyl]-ceph-3-em-4-carboxylate A mixture of 7.44 g (20 mmoles) of 7-tert.-butoxy-carbonylaminocephalosporanic acid, 66 g (0.4 mole) of potassium iodide, 15 g (0.14 mole) of 4-ethylpyridine and 30 ml of water was stirred for 6 hours at 75° C. The mixture was chromatographed over silica gel in a manner analogous to Example 1. The title compound was eluted with acetone/water (3:1). Yield: 2.4 g (30% of theory) of an amorphous product, after freeze-drying.

NMR (D$_6$-DMSO): δ=1.05–1.48 (s,t,9H,tert.-butyl and 3H,CH$_2$CH$_3$); 2.7–3.72 (2H,SCH$_2$ and H$_2$O); 4.02–5.62 (m,6H,CH$_2$CH$_3$, 2 lactam-H and CH$_2$N); 7.63–9.44 ppm (m,5H,NH and 4Py-H).

IR (KBr): 1780 (lactam-CO), 1710 cm$^{-1}$ (ester).

c) 7-Amino-3-[(4-ethyl-1-pyridinium)-methyl]-ceph-3-em-4-carboxylate

A solution of 2.10 g (5 mmoles) of 7-tert.butoxycarbonylamino-3-[(4-ethyl-1-pyridinium)-methyl]-ceph-3-em-4-carboxylate in 20 ml of trifluoroacetic acid and 0.2 ml of anisole was left for 30 minutes at 10°–20° C. After trifluoroacetic acid had been distilled off, crystallization was induced in the residue by repeatedly triturating it with ether. The crystals were dissolved in 5 ml of water with the aid of sodium bicarbonate and the solution was chromatographed with water over a Servachrom XAD-2 adsorbent resin (2×40 cm column). The title compound was eluted after a forerun of 400 ml. The product fractions were freeze-dried, and 1.65 g (78% of theory) of a colorless solid were obtained.

NMR (CF$_3$COOD): δ=1.47 (t,J=7 Hz,3H,CH$_2$CH$_3$); 3.03 (q,J=7 Hz,2H,CH$_2$ CH$_3$); 3.60 and 3.78 (AB,J=19 Hz, 2H,SCH$_2$), 5.25–5.72 (m,4H, 2 lactam-H and 5.25 CH$_2$N), 7.75 and 8.63 ppm (AA'BB',J=6 Hz,4Py-H).

IR (KBr): 1785 cm$^{-1}$ (lactam-CO).

d) 7-[2-(2-Aminothiazol-4-yl)-2-syn-methoxyiminoacetamido]-3-[(4-ethyl-1-pyridinium)-methyl]-ceph-3-em-4-carboxylate 1 g (5 mmoles) of 2-(2-amino-1,3-thiazol-4-yl)-2-syn-methoxyiminoacetic acid was suspended in 20 ml of methylene chloride. After the addition of 0.93 ml (10 mmoles) of N,N-dimethylacetamide, the mixture was cooled down to −5°, and a solution of 0.75 g (7.5 mmoles) of phosgene in 5 ml of toluene was added dropwise with stirring. The resulting mixture was stirred for 2 hours at −5° C., and after the mixture had been cooled down to −10° C. a cooled mixture at −10° C. of 1.60 g (3.8 mmoles) of 7-amino-3-[(4-ethyl-1-pyridinium)-methyl]-ceph-3-em-4-carboxylate, 1.1 ml (8 mmoles) of triethylamine, 2 g (10 mmoles) of bis-trimethylsilylacetamide and 20 ml of N,N-dimethylacetamide was added. The resulting mixture was stirred for 2 hours at −10° C., 30 ml of ice water were added, and stirring was continued for a further 30 minutes at 0°–5° C. and for 1 hour without cooling. The solvent was removed in vacuo, and the residue was chromatographed over silica gel with acetone/water (3:1) in a manner analogous to Example 1. Freeze-drying produced the title compound in a yield of 60%. The compound was in all respects identical to the compound of Example 1.

EXAMPLES 58–107

The compounds of Tables 3 and 4 were prepared from the corresponding 7-amino-ceph-3-em-4-carboxylate derivatives (general formula III, prepared analogously to Example 57 b and c) and 2-(2-amino-1,3-thiazol-4-yl)-2-syn-methoxyiminoacetic acid in a manner analogous to Example 57 d. The compounds were identical in all respects to those of Tables 3 and 4.

EXAMPLE 108

3-[(4-Cyclopropyl-1-pyridinium)-methyl]-7-[2-syn-methoxyimino-2-(2-aminothiazol-4-yl)-acetamido]-ceph-3-em-4-carboxylate (Process a)

The pH of a mixture of 4.55 g (10 mmoles) of 7-[(2-aminothiazol-4-yl)-2-syn-methoxyimino-acetamido]-cephalosporanic acid, 1 g (10 mmoles) of potassium bicarbonate and 2.38 g (20 mmoles) of 4-cyclopropylpyridine in 25 ml of water was adjusted by the addition of 1.5 ml of 2N acetic acid to a value of 6.5 and the mixture was then heated for 3 hours with stirring at 60°–63° C. After the batch had cooled down, it was diluted with 50 ml of acetone and chromatographed over 400 g of silica gel (Merck 0.063–0.2 mm) with acetone/water (2:1). After a forerun of 800 ml, the title compound was eluted. The freeze-dried crude product was rechromatographed over a "Lobar C" column (Merck) with acetone/water (2:1). Freeze-drying the product fractions produced 1 g (19.5% of theory) of a colorless amorphous solid.

$^1$H-NMR (CF$_3$CO$_2$D): δ=1.17–2.51 (m, 5H, cyclopropyl); 3.48 and 3.76 (AB,J=19 Hz, 2H, SCH$_2$); 4.24

(s, 3H, OCH₃); 5.12-6.19 (m, 4H, CH₂Py and 2 lactam-H); 7.41 (s, 1H, thiazole); 7.65 and 8.68 ppm (AA'BB', J=7 Hz, 4H, Py).

(Process b)

A mixture of 5 g (25 mmoles) of 2-(2-amino-1,3-thiazol-4-yl)-2-syn-methoxyiminoacetic acid, 3.8 g (25 mmoles) of 1-hydroxy-1H-benzotriazole hydrate, 5.7 g (27.5 mmoles) of dicyclohexylcarbodiimide and 125 ml of N,N-dimethylformamide was stirred for 3 hours at room temperature. The mixture was filtered and the filtrate was cooled down to 0° C. and added to a solution of 10.1 g (25 mmoles) of 7-amino-3-[(4-cyclopropyl-1-pyridinium)-methyl]-ceph-3-em-4-carboxylate dihydrochloride, 50 ml of N,N-dimethylformamide and 8 ml (63.5 mmoles) of N,N-dimethylaniline. The mixture was left overnight at room temperature, the precipitate was filtered off with suction, and the filtrate was added dropwise with stirring to 1.5 l of diethyl ether. The amorphous precipitate was stirred together with acetone, filtered off with suction and washed with acetone. This crude product was dissolved in 200 ml of water, a small amount of undissolved material was filtered off, and the aqueous solution was freeze-dried. 8.8 g (68% of theory) of a colorless solid were obtained. The compound was in all respects identical to the compound obtained above according to process a).

EXAMPLE 109

3-[(3,4-Dihydro-2H-pyrano[3,2-c]pyridinium)-methyl]-7-[2-syn-methoxyimino-2-(2-aminothiazol-4-yl)-acetamido]ceph-3-em-4-carboxylate A mixture of 6.83 g (15 mmoles) of 7-[2-aminothiazol-4-yl)-2-syn-methoxyimino-acetamido]-cephalosporanic acid, 1.5 g (15 mmoles) of potassium bicarbonate, 24 g (0.25 mole) of potassium thiocyanate, 25 ml of water and 3.4 g (25 mmoles) of 3,4-dihydro-2H-pyrano[3,2-c]pyridine (H. Sliwa and G. Cordonnier, J. Het. Chemistry 12, 809 (1975)), the pH of which had been adjusted by the addition of 2.4 g of 85% strength phosphoric acid to a value of 6.8, was stirred for 2 hours at 68°-70° C. After the batch had cooled down, 200 ml of acetone were added, and the mixture was chromatographed over 400 g of silica gel (Merck 0.063-0.2 mm). The salts were eluted with acetone/water (8:1), and the product was eluted with acetone/water (2:1). The product fractions were lyophilized, and the lyophilizate was rechromatographed over a "Lobar C" column (Merck AG) with acetone/water (2:1). Freeze-drying the product fractions produced 0.9 g of the title compound in the form of a colorless solid.

¹H-NMR (CF₃CO₂D): δ=2.00-2.45 (m, 2H, pyran-H); 2.75-3.30 (m, 2H, pyran-H), 3.52 and 3.75 (AB, J=19 Hz, 2H, SCH₂); 4.25 (s, 3H, OCH₃); 4.4-4.85 (m, 2H, pyran-H); 5.15-6.2 (m, 4H, CH₂Py and 2-lactam-H); 7.35-7.45 (m, 1Py-H and 1-thiazole-H); 8.3-8.65 ppm (m, 2H, Py).

The compounds which are listed below, correspond to the general formula I in which R¹ denotes hydrogen and R² denotes methyl and, in the pyridinium radical (A in the formula I), carry the substituents indicated in the second column of Table 5, were obtained in a manner analogous to Example 109. The numeral attached to the substituents indicates in each case the exact position of the substituent(s) in the pyridinium radical.

TABLE 5

| Example | Substituent | Yield % of theory | ¹H-NMR: δ (ppm) |
|---|---|---|---|
| 110 | 3-iso-C₃H₇ | 22 | (CF₃CO₂D): 1.44(d, J=7Hz, 6H, CH(CH₃)₂); 3.04-4.08 (m, 3H, CH(CH₃)₂ and SCH₂); 4.22(s, 3H, OCH₃); 5.26-5.29(m, 4H, CH₂—Py and 2 lactam-H); 7.38(s, 1H, thiazole); 7.91-8.84(m, 4H, Py) |
| 111 | 2-CH₃-5-CH₃ | 23 | (CF₃CO₂D): 2.59(s, 3H, PyCH₃); 2.93(s, 3H, PyCH₃); 3.46 and 3.66(AB, J=19Hz, 2H, SCH₂); 4.25(s, 3H, OCH₃); 5.36-6.13(m, 4H, CH₂Py and 2 lactam-H); 7.40 (s, 1H, thiazole); 7.77-8.65(m, 3H, Py) |
| 112 | 2-CH₃-4-CH₃ | 17 | (CF₃CO₂D): 2.70(s, 3H, CH₃); 2.91(s, 3H, CH₃); 3.47 and 3.67(AB, J=19Hz, 2H, SCH₂); 4.24(s, 3H, OCH₃); 5.34-6.11(m, 4H, CH₂Py and 2 lactam-H); 7.37(s, 1H, thiazole); 7.65-8.56(m, 3H, Py) |
| 113 | 2-CH(C₂H₅)₂ | 28 | (CF₃CO₂D): 0.80-2.24(m, 10H, CH(C₂H₅)₂); 3.17-3.97 (m, 3H, CH(C₂H₅)₂ and SCH₂); 4.25(s, 3H, OCH₃); 5.14-6.12(m, 4H, CH₂Py and 2 lactam-H); 7.40(s, 1H, thiazole); 7.80-8.90(m, 4H, Py) |
| 114 | 3-CH₃-4-C₂H₅ | 18 | (CF₃CO₂D): 1.44(t, J=7Hz, 3H, CH₂CH₃); 2.59(s, 3H, PyCH₃); 3.03(q, J=7Hz, CH₂CH₃); 3.50 and 3.76(AB, J=19Hz, 2H, SCH₂); 4.23(s, 3H, OCH₃); 5.16-6.26(m, 4H, CH₂Py and 2 lactam-H); 7.41(s, 1H, thiazole); 7.93 and 8.66(AA'BB', J=6Hz, 3H, Py) |
| 115 | 4-CH₂C₆H₅ | 8 | (CF₃CO₂D): 3.46 and 3.77(AB, J=18Hz, 2H, SCH₂); 4.22 (s, 3H, OCH₃); 4.32(s, 2H, CH₂C₆H₅); 5.13-6.19(m, 4H, CH₂—Py and 2 lactam-H); 7.05-7.46(m, 6H, C₆H₅ and thiazole); 7.81 and 8.78(AA'BB', J=6Hz, 4H, Py) |
| 116 | 4-CH₂-p-C₆H₄Cl | 7 | (CF₃CO₂D): 3.47 and 3.78(AB, J=18Hz, 2H, SCH₂); 4.24(s, 3H, OCH₃); 4.33(s, 2H, CH₂C₆H₄); 5.18-6.23 (m, 4H, CH₂Py and 2 lactam-H); 7.05-7.46(m, 5H, C₆H₄ and thiazole); 7.87 and 8.83(AA'BB', J=6Hz, 4H, Py) |

TABLE 5-continued

| Example | Substituent | Yield % of theory | $^1$H-NMR: δ (ppm) |
|---|---|---|---|
| 117 | 3-(phenyl) | 11 | (CF$_3$CO$_2$D): 3.57 and 3.85(AB, J=19Hz, 2H, SCH$_2$); 4.22(s, 3H, OCH$_3$); 5.36-6.39(m, 4H, CH$_2$Py and 2 lactam-H); 7.39(s, 1H, thiazole); 7.63(s, 5H, C$_6$H$_5$); 8.03-9.20(m, 4H, Py) |
| 118 | 3-CH$_2$-CH=CH$_2$ | 21 | (CF$_3$CO$_2$D): 3.23-4.07(m, 4H, CH—C$\underline{H}_2$ and SCH$_2$); 4.23 (s, 3H, OCH$_3$); 5.09-6.31(m, 7H, C$\underline{H}$=C$\underline{H}_2$, CH$_2$Py and 2 lactam-H); 7.38(s, 1H thiazole); 7.91-8.93(m, 4H, Py) |
| 119 | 3-CH$_2$—C(CH$_3$)=CH$_2$ | 20 | (CF$_3$CO$_2$D): 1.79(s, 3H, CCH$_3$); 3.21-4.23(m, 7H, SCH$_2$, CH$_2$C and OCH$_3$); 4.80-6.31(m, 6H, C=CH$_2$, CH$_2$Py and 2 lactam-H); 7.40(s, 1H, thiazole); 7.92-8.91(m, 4H, Py) |
| 120 | 3-CH=CH—CH$_3$ | 23 | (CF$_3$CO$_2$D): 2.06(d, J=6Hz, 3H, CH—C$\underline{H}_3$); 3.51 and 3.80(AB, J=19Hz, 2H, SCH$_2$); 4.23(s, 3H, OCH$_3$); 5.22-6.79(m, 6H, CH=CH, CH$_2$Py and 2 lactam-H); 7.42(s, 1H, thiazole); 7.86-8.82(m, 4H, Py) |
| 121 | 4-CH$_2$—CH$_2$—CH=CH$_2$ | 23 | (CF$_3$CO$_2$D): 2.40-3.27(m, 4H, CH$_2$—CH$_2$); 3.48 and 3.78 (AB, J=19Hz, 2H, SCH$_2$); 4.24(s, 3H, OCH$_3$); 4.90-6.24(m, 7H, CH=CH$_2$, CH$_2$Py and 2 lactam-H); 7.41(s, 1H, thiazole); 7.96 and 8.81(AA'BB', J=6Hz, 4H, Py) |
| 122 | 5-OH-2-CH$_3$ | 13 | (CF$_3$CO$_2$D): 2.86(s, 3H, PyCH$_3$); 3.51 and 3.72(AB, J=18Hz, 2H, SCH$_2$); 4.26(s, 3H, OCH$_3$); 5.37-6.13 (m, 4H, CH$_2$Py and 2 lactam-H); 7.41(s, 1H, thiazole); 7.66-8.39(m, 3H, Py) |
| 123 | 3-OH-4-CH$_3$ | 22 | (CF$_3$CO$_2$D): 2.60(s, 3H, CH$_3$); 3.45 and 3.80 (AB, J= 19Hz, 2H, SCH$_2$); 4.23(s, 3H, OCH$_3$); 5.15-6.25(m, 4H, CH$_2$Py and 2 lactam-H); 7.41(s, 1H, thiazole); 7.70-8.75(m, 3H, Py) |
| 124 | 4-CH(OH)—C$_2$H$_5$ | | (CF$_3$CO$_2$D): 1.13(t, J=7Hz, 3H, CH$_3$); 1.90-2.28(m, 2H, C$\underline{H}_2$CH$_3$); 3.53 and 3.81(AB, J=19Hz, 2H, SCH$_2$); 4.23(s, 3H, OCH$_3$); 5.07-6.27(m, 5H, C$\underline{H}$OH, CH$_2$Py and 2 lactam-H); 7.38(s, 1H, thiazole); 8.15 and 8.94(AA'BB', J=6Hz, 4H, Py) |
| 125 | 3-CH(OH)—C$_2$H$_5$ | 14 | (CF$_3$CO$_2$D): 1.11(t, J=7Hz, 3H, CH$_3$); 1.93-2.28(m, 2H, C$\underline{H}_2$CH$_3$); 3.55 and 3.82(AB, J=19Hz, 2H, SCH$_2$); 4.23(s, 3H, OCH$_3$); 5.07-6.34(m, 5H, C$\underline{H}$OH, CH$_2$Py and 2 lactam-H); 7.39(s, 1H, thiazole); 8.01-9.14(m, 4H, Py) |
| 126 | 3-CH$_2$—C(CH$_3$)$_2$—OH | 28 | (CF$_3$CO$_2$D): 1.47(s, 6H, C(CH$_3$)$_2$); 3.23(bs, 2H, PyCH$_2$); 3.54 and 3.81(AB, J=19Hz, 2H, SCH$_2$); 4.24(s, 3H, OCH$_3$); 5.29-6.33(m, 4H, CH$_2$Py and 2 lactam-H); 7.41 (s, 1H, thiazole); 7.96-9.00(m, 4H, Py) |
| 127 | 2-CH$_2$OH-4-CH$_3$ | 21 | (CF$_3$CO$_2$D): 2.75(s, 3H, CH$_3$); 3.45 and 3.75(AB, J= 19Hz, 2H, SCH$_2$); 4.23(s, 3H, OCH$_3$); 5.15-6.20(m, 6H, CH$_2$Py, C$\underline{H}_2$OH and 2 lactam-H); 7.41(s, 1H, thiazole); 7.60-8.75(m, 3H, Py) |
| 128 | 2-CH(CH$_2$CH$_2$OH)$_2$ | 8 | (CF$_3$CO$_2$D): 3.35-4.57(m, 10H, CH, SCH$_2$, 2C$\underline{H}_2$OH, OCH$_3$); 5.25-6.25(m, 4H, CH$_2$Py, 2 lactam-H); 7.42(s, 1H, thiazole); 7.85-8.95(m, 4H, Py) |
| 129 | 4-CH$_2$CH(OH)CH$_3$ | 14 | (CF$_3$CO$_2$D): 1.52(d, J=7Hz, 3H, CH$_3$); 3.10-4.00(m, 4H, PyCH$_2$ and SCH$_2$); 4.00-4.60(m, 4H, OCH$_3$— singlet and CH); 5.25-6.35(m, 4H, CH$_2$Py and 2 lactam-H); 7.41(s, 1H, thiazole); 8.07 and 8.90(AA'BB', J=6Hz, 4H, Py) |
| 130 | 4-CH$_2$—CH$_2$—CH$_2$—OH | 14 | (CF$_3$CO$_2$D): 2.02-2.48(m, 2H, CH$_2$C$\underline{H}_2$); 2.97-4.23(m, 9H, PyCH$_2$, CH$_2$O, SCH$_2$ and OCH$_3$); 5.27-6.27(m, 4H, CH$_2$Py and 2 lactam-H); 7.39(s, 1H, thiazole); 7.97 and 8.85 (AA'BB', J=6Hz, 4H, Py) |
| 131 | 3-(cyclohexyl) | 27 | (CF$_3$CO$_2$D): 1.29-2.17(m, 10H, cyclohexyl); 2.67-4.08(m, 3H, cyclohexyl and SCH$_2$); 4.23(s, 3H, OCH$_3$); 5.22-6.39 (m, 4H, CH$_2$Py and 2 lactam-H); 7.39(s, 1H, thiazole); 8.03-9.21(m, 4H, Py) |

TABLE 5-continued

| Example | Substituent | Yield % of theory | $^1$H-NMR: δ (ppm) |
|---|---|---|---|
| 132 | 4-cyclohexyl | 28 | (CF$_3$CO$_2$D): 1.23–2.24(m, 10H, CH$_2$-cyclohexyl); 2.82–4.10 (m, 3H, CH-cyclohexyl, SCH$_2$); 4.23(s, 3H, OCH$_3$); 5.18–6.23 (m, 4H, CH$_2$Py and 2 lactam-H); 7.39(s, 1H, thiazole); 7.93 and 8.82(AA'BB', J=6Hz, 4H, Py) |
| 133 | 3-cyclopentyl | 19 | (CF$_3$CO$_2$D): 1.38–4.23(m, 14H, cyclopentyl, SCH$_2$ and OCH$_3$); 5.23–6.30(m, 4H, CH$_2$Py and 2 lactam-H); 7.39(s, 1H, thiazole); 7.88–8.83(m, 4H, Py) |
| 134 | 4-cyclohexenyl | 26 | (CF$_3$CO$_2$D): 1.71–2.68(m, 8H, cyclohexenyl), 3.53–3.77(AB, J=19Hz, 2H, SCH$_2$); 4.23(s, 3H, OCH$_3$), 5.14–6.19(m, 4H, CH$_2$Py and 2 lactam-H); 7.16(bs, 1H, cyclohexenyl) 7.40 (s, 1H, thiazole); 8.03 and 8.69(AA'BB', J=7Hz, 4H, Py) |
| 135 | 3-cyclohexenyl | 25 | (CF$_3$CO$_2$D): 1.69–2.04(bs, 4H, cyclohexenyl); 2.21–2.60(m, 4H, cyclohexenyl); 3.51 and 3.80(AB, J=19Hz, 2H, SCH$_2$); 4.23(s, 3H, OCH$_3$); 5.24–6.28(m, 4H, CH$_2$Py and 2 lactam-H); 6.51–6.73(m, 1H, cyclohexenyl); 7.37(s, 1H, thiazole); 7.85–8.93(m, 4H, Py) |
| 136 | 4-cyclopentenyl | 20 | (CF$_3$CO$_2$D): 1.99–3.03(m, 6H, cyclopentenyl); 3.50 and 3.77(AB, J=19Hz, 2H, SCH$_2$); 4.24(s, 3H, OCH$_3$); 5.15–6.19(m, 4H, CH$_2$Py and 2 lactam-H); 7.22(bs, 1H, cyclopentenyl); 7.41(s, 1H, thiazole); 7.99 and 8.70(AA'BB', J=6Hz, 4H, Py) |
| 137 | 3-cyclopentenyl | 18 | (CF$_3$CO$_2$D): 2.03–3.03(m, 6H, cyclopentenyl); 3.53 and 3.81 (AB, J=19Hz, 2H, SCH$_2$); 4.23(s, 3H, OCH$_3$); 5.28–6.32 (m, 4H, CH$_2$Py and 2 lactam-H); 6.79(bs, 1H, cyclopentenyl); 7.41(s, 1H, thiazole); 7.89–8.97(m, 4H, Py) |
| 138 | 3-cycloheptenyl | 23 | (CF$_3$CO$_2$D): 1.55–2.06(m, 6H, cycloheptenyl); 2.33–2.84 (m, 4H, cycloheptenyl); 3.51 and 3.80(AB, J=19Hz, 2H, SCH$_2$); 4.23(s, 3H, OCH$_3$), 5.24–6.61(m, 5H, CH$_2$Py, 2 lactam-H and cycloheptenyl-H); 7.39(s, 1H, thiazole); 7.85–8.86(m, 4H, Py) |
| 139 | 3-methylcyclohexenyl | 16 | (CF$_3$CO$_2$D): 1.04–2.69(m, 10H, methylcyclohexenyl); 3.52 and 3.80(AB, J=19Hz, 2H, SCH$_2$); 4.23(s, 3H, OCH$_3$); 5.24–6.32(m, 4H, CH$_2$Py and 2 lactam-H); 6.62(m, 1H, methylcyclohexenyl); 7.40(s, 1H, thiazole); 7.85–8.94 (m, 4H, Py) |
| 140 | 3-hydroxycyclohexyl | 20 | (CF$_3$CO$_2$D): 1.68–2.21(bs, 10H, cyclohexyl); 3.55 and 3.79(AB, J=19Hz, 2H, SCH$_2$); 4.23(s, 3H, OCH$_3$); 5.34–6.27(m, 4H, CH$_2$Py and 2 lactam-H); 7.37(s, 1H, thiazole); 7.37–9.29(m, 4H, Py) |
| 141 | 3-hydroxycyclopentyl | 18 | (CF$_3$CO$_2$D): 2.19(bs, 8H, cyclopentyl); 3.54 and 3.82(AB, J=19Hz, 2H, SCH$_2$); 4.23(s, 3H, OCH$_3$), 5.35–6.30(m, 4H, CH$_2$Py and 2 lactam-H); 7.37(s, 1H, thiazole); 7.97–9.30 (m, 4H, Py) |
| 142 | 4-hydroxycyclohexyl | 22 | (CF$_3$CO$_2$D): 1.95(bs, 10H, cyclohexyl); 3.51 and 3.83(AB, J=19Hz, 2H, SCH$_2$); 4.24(s, 3H, OCH$_3$); 5.24–6.26(m, 4H, CH$_2$Py and 2 lactam-H); 7.39(s, 1H, thiazole); 8.27 and 8.93 (AA'BB', J=6Hz, 4H, Py) |
| 143 | 4-hydroxycyclopentyl | 15 | (CF$_3$CO$_2$D): 2.17(bs, 8H, cyclopentyl); 3.52 and 3.82(AB, J=19Hz, 2H, SCH$_2$); 4.23(s, 3H, OCH$_3$); 5.26–6.28(m, 4H, CH$_2$Py and 2 lactam-H); 7.39(s, 1H, thiazole); 8.25 and 8.91 (AA'BB', J=7Hz, 4H, Py) |
| 144 | 3-hydroxycycloheptyl | 21 | (CF$_3$CO$_2$D): 1.84(bs, 8H, cycloheptyl); 2.17(bs, 4H, cycloheptyl); 3.54 and 3.81(AB, J=19Hz, 2H, SCH$_2$); 4.23(s, 3H, OCH$_3$); 5.35–6.29(m, 4H, CH$_2$Py and 2 lactam-H); 7.38 (s, 1H, thiazole); 7.97–9.28(m, 4H, Py) |

TABLE 5-continued

| Example | Substituent | Yield % of theory | $^1$H-NMR: δ (ppm) |
|---|---|---|---|
| 145 | 3-OH, 4-CH$_3$ cyclohexyl | 16 | (CF$_3$CO$_2$D): 0.98–2.48(m, 12H, methylcyclohexyl); 3.56 and 3.80(AB, J=19Hz, 2H, SCH$_2$); 4.23(s, 3H, OCH$_3$); 5.36–6.30(m, 4H, CH$_2$Py and 2 lactam-H); 7.39(s, 1H, thiazole); 7.92–9.32(m, 4H, Py) |
| 146 | 4-CH$_2$-(1-OH cyclopentyl) | 17 | (CF$_3$CO$_2$D): 1.91(bs, 8H, cyclopentyl); 3.39(bs, 2H, PyCH$_2$); 3.58 and 3.82(AB, J=19Hz, 2H, SCH$_2$); 4.24(s, 3H, OCH$_3$); 5.23–6.27(m, 4H, CH$_2$Py and 2 lactam-H); 7.42(s, 1H, thiazole); 8.08 and 8.87(AA'BB', J=6Hz, 4H, Py) |
| 147 | 4-CH$_2$-(1-OH cyclohexyl) | 22 | (CF$_3$CO$_2$D): 1.71(bs, 10H, cyclohexyl); 3.27(bs, 2H, PyCH$_2$); 3.59 and 3.81(AB, J=19Hz, 2H, SCH$_2$); 4.23(s, 3H, OCH$_3$); 5.19–6.25(m, 4H, CH$_2$Py and 2 lactam-H); 7.42(s, 1H, thiazole); 8.03 and 8.86(AA'BB', J=6Hz, 4H, Py) |
| 148 | 4-tetrahydropyranyl | 21 | (CF$_3$CO$_2$D): 1.83–2.30(m, 4H, pyranyl); 3.03–4.66)(m, 10H, pyranyl, SCH$_2$ and OCH$_3$); 5.21–6.26(m, 4H, CH$_2$Py and 2 lactam-H); 7.39(s, 1H, thiazole); 8.01 and 8.93(AA'BB', J=6Hz, 4H, Py) |
| 149 | 4-OCH$_3$-3-CH$_3$ | 18 | (CF$_3$CO$_2$D): 2.40(s, 3H, CH$_3$); 3.45 and 3.77(AB, J=19Hz, 2H, SCH$_2$); 4.24(bs, 6H, 2×OCH$_3$); 5.03–6.20(m, 4H, CH$_2$Py and 2 lactam-H); 7.41(s, 1H, thiazole); 7.38(d, J=7Hz, 1H, Py); 8.35–8.85(m, 2H, Py) |
| 150 | 3-OCH$_3$-4-CH$_3$ | 23 | (CF$_3$CO$_2$D): 2.60(s, 3H, CH$_3$); 3.45 and 3.82(AB, J=19Hz, 2H, SCH$_2$); 4.13(s, 3H, OCH$_3$); 4.23(s, 3H, OCH$_3$); 5.15–6.30(m, 4H, CH$_2$Py and 2 lactam-H); 7.41(s, 2H, thiazole); 7.72–8.60(m, 3H, Py) |
| 151 | 3-OCH$_3$ | 21 | (CF$_3$CO$_2$D): 3.50 and 3.83(AB, J=19Hz, 2H, SCH$_2$); 4.12 (s, 3H, OCH$_3$); 4.24(s, 3H, OCH$_3$); 5.17–6.40(m, 4H, (CH$_2$Py and 2 lactam-H); 7.42(s, 1H, thiazole); 7.95–8.80 (m, 4H, Py) |
| 152 | 4-OC$_2$H$_5$ | 18 | (CF$_3$CO$_2$D): 1.60(t, J=7Hz, 3H, CH$_3$); 3.45 and 3.80(AB, J=19Hz, 2H, SCH$_2$); 4.24(s, 3H, OCH$_3$); 4.30(q, J=7Hz, CH$_2$CH$_3$); 5.00–6.20(m, 4H, CH$_2$Py and 2 lactam-H); 7.41(s, 1H, thiazole); 7.40 and 8.70(AA'BB', J=6Hz, 4H, Py) |
| 153 | 3-OC$_2$H$_5$ | 24 | (CF$_3$CO$_2$D): 1.56(t, J=7Hz, 3H, CH$_3$); 3.46 and 3.82(AB, J=19Hz, 2H, SCH$_2$); 4.30(q, J=7Hz, CH$_2$CH$_3$); 4.24(s, 3H, OCH$_3$); 5.15–6.35(m, 4H, CH$_2$Py and 2 lactam-H); 7.41(s, 1H, thiazole); 7.90–8.75(m, 4H, Py) |
| 154 | 3-OCH(CH$_3$)$_2$ | 17 | (CF$_3$CO$_2$D): 1.45 and 1.55(d, J=6Hz, 6H, 2CH$_3$); 3.45 and 3.85(AB, J=19Hz, 2H, SCH$_2$); 4.24(s, 3H, OCH$_3$); 4.85 (m, 1H, CH); 5.15–6.35(m, 4H, CH$_2$Py and 2 lactam-H); 7.41 (s, 1H, thiazole); 7.85–8.70(m, 4H, Py) |
| 155 | 3-OCH$_2$CH$_2$CH$_3$ | 19 | (CF$_3$CO$_2$D): 1.11(t, J=7Hz, 3H, CH$_3$) 1.62–2.35(m, 2H, CH$_2$); 3.50 and 3.82(AB, J=19Hz, 2H, SCH$_2$); 4.00–4.45(m, 5H, CH$_2$ and OCH$_3$); 5.15–6.35(m, 4H, CH$_2$Py and 2 lactam-H); 7.41(s, 1H, thiazole); 7.90–8.75(m, 4H, Py) |
| 156 | 2-CH$_2$—CH$_2$—O—CH$_3$ | 18 | (CF$_3$CO$_2$D): 3.24–4.50(m, 10H, CH$_2$—CH$_2$, OCH$_3$ and OCH$_3$); 5.05–6.15(m, 4H, CH$_2$Py and 2 lactam-H); 7.40(s, 1H, thiazole); 7.80–8.83(m, 4H, Py) |
| 157 | 4-CH$_2$—CH$_2$OC$_2$H$_5$ | 12 | (CF$_3$CO$_2$D): 1.33(t, J=7Hz, 3H, CH$_3$); 3.27–4.40(m, 11H, 3CH$_2$, SCH$_2$, OCH$_3$); 5.15–6.30(m, 4H, CH$_2$Py, 2 lactam-H); 7.42(s, 1H, thiazole); 8.07 and 8.90(AA'BB', J=6Hz, 4H, Py) |
| 158 | 2-CH$_2$—CH$_2$—O—C$_2$H$_5$ | 20 | (CF$_3$CO$_2$D): 1.33(t, J=7Hz, 3H, CH$_2$CH$_3$); 3.49–4.26(m, 11H, 3CH$_2$, SCH$_2$, OCH$_3$); 5.38–6.20(m, 4H, CH$_2$Py and 2 lactam-H); 7.42(s, 1H, thiazole); 7.88–8.86(m, 4H, Py) |
| 159 | 4-COCH$_3$ | 17 | (CF$_3$CO$_2$D): 2.90(s, 3H, CH$_3$); 3.55 and 3.85(AB, J=19Hz, 2H, SCH$_2$); 4.24(s, 3H, OCH$_3$); 5.25–6.50(m, 4H, CH$_2$Py 2 lactam-H); 7.41(s, 1H, thiazole); 8.57 and 9.30(AA'BB', J=6Hz, 4H, Py) |
| 160 | 4-CH$_2$COCH$_3$ | 12 | (CF$_3$CO$_2$D): 2.53(s, 3H, CH$_3$); 3.50 and 3.85(AB, J=19Hz, 2H, SCH$_2$); 4.00–4.45(m, 5H, CH$_2$ and OCH$_3$); 5.20–6.35(m, 4H, CH$_2$Py and 2 lactam-H); 7.41(s, 1H, thiazole); 8.02 and 8.95(AA'BB', J=6Hz, 4H, Py) |

TABLE 5-continued

| Example | Substituent | Yield % of theory | $^1$H-NMR: δ (ppm) |
|---|---|---|---|
| 161 | 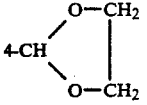 4-CH(O—CH$_2$—O—CH$_2$) | 19 | (CF$_3$CO$_2$D): 3.53 and 3.81(AB, J=19Hz, 2H, SCH$_2$); 4.23(s, 3H, OCH$_3$); 4.26(s, 4H, OCH$_2$) 5.30-6.33(m, 5H, CH$_2$Py, 2 lactam-H and CHO); 7.39(s, 1H, thiazole); 8.26 and 9.04 (AA'BB', J=7Hz, 4H, Py) |
| 162 | 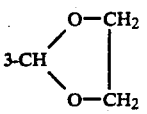 3-CH(O—CH$_2$—O—CH$_2$) | 21 | (CF$_3$CO$_2$D): 3.59 and 3.84(AB, J=19Hz, 2H, SCH$_2$); 4.24(s, 3H, OCH$_3$); 4.30(s, 4H, OCH$_2$); 5.35-6.37(m, 4H, CH$_2$Py and 2 lactam-H); 7.41(s, 1H, thiazole); 8.07-9.21(m, 4H, Py) |
| 163 | 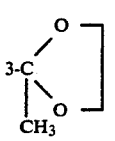 3-C(O—O)(CH$_3$) dioxolane | 18 | (CF$_3$CO$_2$D): 1.85(s, 3H, CH$_3$); 3.55 and 3.85(AB, J=19Hz, 2H, SCH$_2$); 3.90-4.55(m, 4H, dioxolane-H); 4.25(s, 3H, OCH$_3$); 5.30-6.35(m, 4H, CH$_2$Py and 2 lactam-H); 7.43(s, 1H, thiazole); 8.00-8.35(m, 1H, Py); 8.68-9.27(m, 3H, Py) |
| 164 | 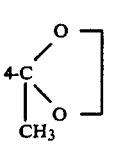 4-C(O—O)(CH$_3$) dioxolane | 19 | (CF$_3$CO$_2$D): 1.83(s, 3H, CH$_3$); 3.50 and 3.90(AB, J=19Hz, 2H, SCH$_2$); 3.90-4.55(m, 4H, dioxolane-H); 4.25(s, 3H, OCH$_3$); 5.20-6.40(m, 4H, CH$_2$Py and 2 lactam-H); 7.43(s, 1H, thiazole); 8.28 and 9.03(AA'BB', J=6Hz, 4H, Py) |
| 165 | 4-CH$_2$—CH$_2$—CH$_2$—Cl | 28 | (CF$_3$CO$_2$D): 2.15-2.48(m, 2H, CH$_2$CH$_2$); 3.04-4.23(m, 9H, PyCH CH$_2$Cl, SCH$_2$, OCH$_3$); 5.21-6.26(m, 4H, CH$_2$Py and 2 lactam-H); 7.39 (s, 1H, thiazole); 7.98 and 8.87(AA'BB', J=6Hz, 4H, Py) |
| 166 | 3-CH$_2$—CH$_2$—CH$_2$—Cl | 16 | (CF$_3$CO$_2$D): 2.13-3.77(m, 8H, Py—CH$_2$—CH$_2$—CH$_2$ and SCH$_2$); 4.23 (s, 3H, OCH$_3$); 5.26-6.33(m, 4H, CH$_2$Py and 2 lactam-H); 7.42 (s, 1H, thiazole); 7.94-8.96(m, 4H, Py) |
| 167 | 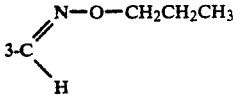 3-C(H)=N—O—CH$_2$CH$_2$CH$_3$ | 29 | (CF$_3$CO$_2$D): 1.03(t, J=7Hz, 3H, CH$_2$CH$_3$); 1.66-2.01(m, 2H, CH$_2$CH$_3$); 3.24-4.45(m, 7H, SCH$_2$, OCH$_2$ and OCH$_3$); 5.30-6.37 (m, 4H, CH$_2$Py and 2 lactam-H); 7.41(s, 1H, thiazole); 7.33-9.20(m, 5H, Py and CH) |
| 168 | 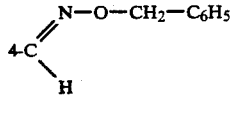 4-C(H)=N—O—CH$_2$—C$_6$H$_5$ | 20 | (CF$_3$CO$_2$D): 3.53 and 3.82(AB, J=19Hz, 2H, SCH$_2$); 4.24 (s, 3H, OCH$_3$); 5.23-6.26(m, 6H, CH$_2$Py, 2 lactam-H and OCH$_2$); 7.37(s, 5H, C$_6$H$_5$); 8.25 and 8.88(AA'BB', J= 7Hz, 4H, Py); 8.28(s, 1H, CH) |
| 169 | 3-CF$_3$ | 9 | (CF$_3$CO$_2$D): 3.55 and 3.90(AB, J=19Hz, 2H, SCH$_2$); 4.23(s, 3H, OCH$_3$); 5.15-6.45(m, 4H, CH$_2$Py and 2 lactam-H); 7.41 (s, 1H, thiazole); 8.15-9.52(m, 4H, Py) |
| 170 | 3-Br-4-CH$_3$ | 17 | (CF$_3$CO$_2$D): 2.80(s, 3H, CH$_3$); 3.50 and 3.85(AB, J=19Hz, 2H, SCH$_2$); 4.23(s, 3H, OCH$_3$); 5.10-6.40(m, 4H, CH$_2$Py and 2 lactam-H); 7.41(s, 1H, thiazole); 7.89(d, J=6Hz, 1H, Py); 8.70-9.20(m, 2H, Py) |
| 171 | 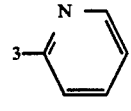 3-pyridyl | 16 | (CF$_3$CO$_2$D); 3.60 and 3.95(AB, J=19Hz, 2H, SCH$_2$) 4.23(s, 3H, OCH$_3$); 5.25-6.55(m, 4H, CH$_2$Py and 2 lactam-H); 7.40(s, 1H, thiazole); 8.2-9.85(m, 8H, Py) |
| 172 | 3-CH$_2$—CN | 14 | (CF$_3$CO$_2$D): 3.57 and 3.84(AB, J=19Hz, 2H, SCH$_2$); 4.23(s, 3H, OCH$_3$); 4.33(s, 2H, CH$_2$CN); 5.36-6.41(m, 4H, CH$_2$Py and 2 lactam-H); 7.40(s, 1H, thiazole); 8.08-9.21(m, 4H, Py) |
| 173 | 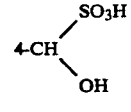 4-CH(SO$_3$H)(OH) | 15 | (CF$_3$CO$_2$D): 3.30-4.11(m, 2H, SCH$_2$); 4.23(s, 3H, OCH$_3$); 5.36-6.46(m, 5H, CH$_2$Py, 2 lactam-H and CH—OH); 7.42(s, 1H, thiazole); 8.73 and 9.30(AA'BB', J=6Hz, 4H, Py) |
| 174 | 4-CH=CH—CO$_2$CH$_3$ | 21 | (CF$_3$CO$_2$D): 3.55 and 3.83(AB, J=19Hz, 2H, SCH$_2$); 4.04 (s, 3H, CO$_2$CH$_3$); 4.24(s, 3H, OCH$_3$); 5.28-6.36(m, 4H, CH$_2$Py and 2 lactam-H); 7.15 and 7.84(AB, J=16Hz, 2H, CH=CH); 7.41(s, 1H, thiazole); 8.25 and 9.01(AA'BB', J=6Hz, 4H, Py) |
| 175 | 3-CH=CH—CO$_2$CH$_3$ | 16 | (CF$_3$CO$_2$D): 3.57 and 3.84(AB, J=19Hz, 2H, SCH$_2$); 4.03 (s, 3H, CO$_2$CH$_3$); 4.23(s, 3H, OCH$_3$); 5.36-6.39(m, 4H, CH$_2$Py and 2 lactam-H); 6.98 and 7.86(AB, J=16Hz, 2H, |

TABLE 5-continued

| Example | Substituent | Yield % of theory | $^1$H-NMR: δ (ppm) |
|---|---|---|---|
| | | | CH=CH); 7.40(s, 1H, thiazole); 8.07-9.21(m, 4H, Py) |

The compounds which are listed below, correspond to the general formula I in which $R^1$ denotes hydrogen and $R^2$ denotes methyl and carry the substituent indicated in the second column of Table 6 as the radical A, were obtained in a manner analogous to Example 109.

and $R^2$ denotes methyl and, in the pyridinium radical (A in the formula I), carry the substituents indicated in the second column of Table 7, were obtained in a manner analogous to Example 109. In Example 191, the radical listed in column 2 denotes the radical A in the formula

TABLE 6

| Example | A | Yield % of theory | $^1$H-NMR δ (ppm) |
|---|---|---|---|
| 176 | | 21 | (CF$_3$CO$_2$D): 2.1-3.9(m, 6H, 4 cyclopentene-H, SCH$_2$); 4.23 (s, 3H, OCH$_3$); 5.1-6.4(m, 5H, CH$_2$Py, cyclopentene-H, 2 lactam-H); 7.42(s, 1H, thiazole); 7.8-8.9(m, 3H, Py) |
| 177 | | 17 | (CF$_3$CO$_2$D): 2.3-3.9(m, 8H, 6 cyclopentene-H), SCH$_2$); 4.23 (s, 3H, OCH$_3$); 5.05-6.3(m, 4H, CH$_2$Py, 2 lactam-H); 7.40 (s, 1H, thiazole); 7.7-8.8(m, 3H, Py) |
| 178 | | 15 | (CF$_3$CO$_2$D): 1.8-2.3(m, 4H, cyclohexene-H); 2.7-3.7(m, 6H, SCH$_2$, cyclohexene-H); 4.23(s, 3H, OCH$_3$); 5.05-6.3(m, 4H, CH$_2$Py, 2 lactam-H); 7.41(s, 1H, thiazole); 7.6-8.7(m, 3H, Py) |
| 179 | | 18 | (CF$_3$CO$_2$D): 1.8-2.35(m, 4 cyclohexene-H); 2.55(s, 3H, CH$_3$); 2.9-3.7(m, 6H, SCH$_2$ and 4 cyclohexene-H); 4.24(s, 3H, OCH$_3$); 5.3-6.25(m, 4H, CH$_2$Py, 2 lactam-H); 7.41(s, 1H, thiazole); 8.12 and 8.42(each 1H, Bs, Py) |
| 180 | | 4 | (CF$_3$CO$_2$D): 3.51 and 3.74(AB, J=19Hz, 2H, SCH$_2$); 4.24(s, 3H, OCH$_3$); 5.35(s, 2H, CH$_2$); 5.1-6.3(m, 4H, CH$_2$Py and 2 lactam-H); 7.41(s, 1H, thiazole); 7.65-9.05(m, 3H, Py) |
| 181 | | 3 | (CF$_3$CO$_2$D): 3.52 and 3.75(AB, J=19Hz, 2H, SCH$_2$); 4.23(s, 3H, OCH$_3$); 5.0-6.3(m, 7H, CH$_2$Py, 2 lactam-H, 3 furan-H); 7.41(s, 1H, thiazole); 7.3-8.9(m, 3H, Py) |
| 182 | | 5 | (CF$_3$CO$_2$D): 3.3-3.8(m, 4H, SCH$_2$ and 2 furan-H); 4.23(s, 3H, OCH$_3$); 4.9-6.4(m, 6H, CH$_2$Py, 2 lactam-H, 2 furan-H, OCH$_2$); 7.42(s, 1H, thiazole); 7.1-8.4(m, 3H, Py) |
| 183 | | 21 | (CF$_3$CO$_2$D): 1.6-2.35(m, 6 cycloheptene-H); 3.0-3.95(m, 6H, 4 cycloheptene-H and SCH$_2$) 4.25(s, 3H, OCH$_3$); 5.25-6.35(m, 4H, CH$_2$Py and 2 lactam-H); 7.42(s, 1H, thiazole); 7.6-8.73 (m, 3H, Py) |

The compounds which are listed below, correspond to the general formula I in which $R^1$ denotes chlorine    I.

TABLE 7

| Example | Substituent | Yield % of theory | $^1$H-NMR: δ (ppm) |
|---|---|---|---|
| 184 | H | 15 | ($CF_3CO_2D$): 3.50 and 3.83(AB, J=19Hz, 2H, $SCH_2$); 4.22(s, 3H, $OCH_3$); 5.40(d, J=5Hz, C-6-H); 5.1–6.4(AB, 2H, $CH_2Py$); 6.08(d, J=5Hz, C-7-H); 7.9–9.2(m, 5H, Py) |
| 185 | 3-$CH_3$ | 13 | ($CF_3CO_2D$): 2.65(s, 3H, $CH_3$); 3.68 and 4.10(AB, J=19Hz, 2H, $SCH_2$); 4.20(s, 3H, $OCH_3$); 5.15–6.30(m, 4H, $CH_2Py$ and 2 lactam-H); 7.8–9.0(m, 4H, Py) |
| 186 | 3,4-Di-$CH_3$ | 15 | ($CF_3CO_2D$): 2.55(s, 3H, $CH_3$); 2.65(s, 3H, $CH_3$); 3.43 and 3.75 (AB, J=19Hz, 2H, $SCH_2$); 4.20(s, 3H, $OCH_3$); 5.1–6.3(m, 4H, $CH_2Py$ and 2 lactam-H); 7.6–8.8(m, 3H, Py) |
| 187 | 2-$CH_2OH$ | 11 | ($CF_3CO_2D$): 3.54 and 3.82(AB, J=19Hz, 2H, $SCH_2$); 4.23 (s, 3H, $OCH_3$); 5.38(s, $CH_2OH$); 5.2–6.3(m, 4H, $CH_2Py$ and 2 lactam-H); 7.9–9.0(m, 3H, Py) |
| 188 | 4-$CH_2OH$ | 21 | ($CF_3CO_2D$): 3.50 and 3.82(AB, J=19Hz, 2H, $SCH_2$); 4.22 (s, 3H, $OCH_3$); 5.25(s, $CH_2OH$); 5.0–6.2(m, 4H, $CH_2Py$ and 2 lactam-H); 8.0–9.1(m, 3H, Py) |
| 189 | 4-$CH_2OCH_3$ | 24 | ($CF_3CO_2D$): 3.2–4.1(AB, J=19Hz, 2H, $SCH_2$); 3.73(s, 3H, $OCH_3$); 4.21(s, 3H, $OCH_3$); 5.00(s, 2H, $\underline{CH_2}$—$OCH_3$); 5.2–6.3 (m, 4H, $CH_2Py$ and 2 lactam-H); 8.0–9.1(AA'BB' J=6hZ, 4H, Py) |
| 190 | 4-$CONH_2$ | 17 | ($CF_3CO_2D$): 3.52 and 3.82(AB, J=19Hz, $SCH_2$); 4.21(s, 3H, $OCH_3$); 5.40(d, 1H, J=5Hz, C-6-H); 5.3–6.5(AB, 2H, $CH_2Py$); 6.08(d, 1H, J=5Hz, C-7-H); 8.57–9.23(AA'BB', J=6Hz, 4H, Py) |
| 191 | (cyclopentene-fused pyridinium) * | 20 | ($CF_3CO_2D$): 2.2–2.8(m, 2H, cyclopentene-H); 3.1–4.2(m, 6H, 4 cyclopentene-H, $SCH_2$); 4.21(s, 3H, $OCH_3$); 5.2–6.2(m, 4H, $CH_2Py$, 2 lactam-H); 7.6–8.6(m, 3H, Py) |

*Radical A in the formula I

EXAMPLES 192-271

The compounds of Tables 5, 6 and 7 were prepared from the corresponding 7-amino-ceph-3-em-4-carboxylic acid derivatives of the general formula III and 2-(2-aminothiazol-4-yl)-2-syn-oxyiminoacetic acids of the general formula IV in a manner analogous to Example 108 (process b). The compounds are in all respects identical to those of Tables 5, 6 and 7.

EXAMPLE 272

3-[(2,3-Cyclopenteno-1-pyridinium)-methyl]-7-[2-syn-hydroxyimino-2-(2-aminothiazol-4-yl)-acetamido]-ceph-3-em-4-carboxylate 4.3 g (10 mmoles) of 2-(2-tritylamino-1,3-thiazol-4-yl)-2-syn-hydroxyiminoacetic acid, 1.68 g (11 mmoles) of 1-hydroxy-1H-benzotriazole hydrate and 2.48 g (12 mmoles) of dicyclohexylcarbodiimide in 70 ml of N,N-dimethylformamide were used to prepare a solution of the activated ester in a manner analogous to Example 108 b. After 3 hours, this mixture was stirred into a cooled solution at $-40°$ of 4.45 g (11 mmoles) of 7-amino-3-[(2,3-cyclopenteno-1-pyridinium)-methyl]-ceph-3-em-4-carboxylate dihydrochloride, 50 ml of N,N-dimethylformamide and 4 ml (32 mmoles) of N,N-dimethylaniline, and the mixture was left overnight at room temperature. Dicyclohexylurea was filtered off, and the yellow-brown filtrate was added dropwise to 1 l of diethyl ether. Supernatant liquid is decanted off, and the precipitate is stirred together with acetone, filtered off with suction, washed with acetone and dried. The crude product (3.5 g) was dissolved in 30 ml of trifluoroacetic acid and the solution was stirred for 25 minutes at room temperature. The volatile constituents were removed in vacuo, and the residue was digested in ether/n-pentane (2:1), filtered off with suction and washed with the same mixture. The precipitate was then dissolved in 5 ml of water with the addition of sodium bicarbonate, and the solution was chromatographed over a "Lobar C" column (Merck) with acetone/water (2:1). Freeze-drying the product fractions produced 1.1 g (22% of theory) of a colorless amorphous solid.

$^1$H-NMR ($CF_3CO_2D$): δ=2.2–2.8 (m, 2H, cyclopentene-H); 3.1–4.1 (m, 6H, cyclopentene-H and $SCH_2$); 5.2–6.3 (m, 4H, $CH_2Py$ and 2 lactam-H); 7.48 (s, 1H, thiazole); 7.6–8.6 ppm (m, 3H, Py).

EXAMPLE 273

3-[(4-Cyclopropyl-1-pyridinium)-methyl]-7-[2-syn-hydroxyimino-2-(2-aminothiazol-4-yl)-acetamido]-ceph-3-em-4-carboxylate From 2-(2-tritylamino-1,3-thiazol-4-yl)-2-syn-hydroxyiminoacetic acid and 7-amino-3-[(4-cylopropyl-1-pyridinium)-methyl]-ceph-3-em-4-carboxylate dihydrochloride by the hydroxybenzotriazole method analogously to Example 272. After elimination of the protective trityl group by means of trifluoroacetic acid and chromatography, the title compound was obtained in the form of a colorless amorphous solid in a yield of 25%.

$^1$H-NMR ($CF_3CO_2D$): δ=1.03–2.6 (m, 5H, cyclopropyl); 3.40 and 3.82 (AB, J=19 Hz, 2H, $SCH_2$); 5.0–6.25 (m, 4H, $CH_2Py$ and 2 lactam-H); 7.50 (s, 1H, thiazole); 7.64 and 8.66 ppm (AA', BB', J=7 Hz, 4H, Py).

The following compounds were prepared in a manner analogous to Example 272 from the 7-amino-ceph-3-em-4-carboxylate dihydrochlorides of the general formula III and the corresponding 2-(2-amino-1,3-thiazol-4-yl)-2-syn-oxyiminoacetic acids of the general formula IV ($R^4$=H).

EXAMPLE 274

3-[(4-Cyclopropyl-1-pyridinium)-methyl]-7-[2-syn-ethoxyimino-2-(2-aminothiazol-4-yl)-acetamido]-ceph-3-em-4-carboxylate Colorless solid, yield 28% of theory.

$^1$H-NMR (CF$_3$CO$_2$D): δ=1.1-2.6 (m, 8H, cyclopropyl and CH$_2$CH$_3$ and 1.43); 3.43 and 3.76 (AB, J=19 Hz, 2H, SCH$_2$) 4.53 (q, J=7 Hz, 2H, CH$_2$CH$_3$); 5.1-6.2 (m, 4H, CH$_2$Py and 2 lactam-H); 7.42 (s, 1H, thiazole); 7.63 and 8.66 ppm (AA', BB', J=7 Hz, 4H, Py).

EXAMPLE 275

3-[(4-Cyclopropyl-1-pyridinium)-methyl]-7-[2-(2-amino-5-bromothiazol-4-yl)-2-syn-methoxyimino-acetamido]-ceph-3-em-4-carboxylate Pale yellow solid, yield 18% of theory.

$^1$H-NMR (CF$_3$CO$_2$D): δ=1.05-2.55 (m, 5H, cyclopropyl); 3.39 and 3.82 (AB, J=19 Hz, 2H, SCH$_2$); 4.22 (s, 3H, OCH$_3$); 5.05-6.23 (m, 4H, CH$_2$Py and 2 lactam-H); 7.58 and 8.66 ppm (AA', BB', J=7 Hz, 4H, Py).

EXAMPLE 276

3-[(4-Cyclopropyl-1-pyridinium)-methyl]-7-[2-syn-ethoxyimino-2-(2-amino-5-chlorothiazol-4-yl)-acetamido]-ceph-3-em-4-carboxylate Colorless solid, yield 20% of theory.

$^1$H-NMR (CF$_3$CO$_2$D): δ=1.06-2.48 (m, 8H, cyclopropyl and —CH$_2$CH$_3$ at 1.42); 3.42 and 3.82 (AB, J=19 Hz, 2H, SCH$_2$); 4.51 (q, J=7 Hz, CH$_2$—CH$_3$); 5.03-6.23 (m, 4H, CH$_2$Py and 2 lactam-H); 7.63 and 8.66 ppm (AA', BB', J=7 Hz, 4H, Py).

EXAMPLE 277

3-[(2,3-Cyclopenteno-1-pyridinium)-methyl]-7-[2-syn-isopropyloxyimino-2-(2-aminothiazol-4-yl)-acetamido]-ceph-3-em-4-carboxylate Colorless solid, yield 23% of theory. $^1$H-NMR (CF$_3$CO$_2$D): δ=1.47 and 1.57 (d, J=6 Hz, 6H, 2 CH$_3$); 2.1-2.8 (m, 2H, cyclopentene-H); 3.0-4.2 (m, 6H, 4 cyclopentene-H and SCH$_2$); 4.8 (m, 1H, CH); 5.1-6.4 (m, 4H, CH$_2$Py and 2-lactam-H); 7.41 (s, 1H, thiazole); 7.5-8.6 ppm (m, 3H, Py).

EXAMPLE 278

3-[(2,3-Cyclopenteno-1-pyridinium)-methyl]-7-[2-syn-propyloxyimino-2-(2-aminothiazol-4-yl)-acetamido]-ceph-3-em-4-carboxylate Colorless solid, yield 21% of theory.

$^1$H-NMR (CF$_3$CO$_2$D): δ=1.08 (t, J=6 Hz, 3H, CH$_3$); 1.6-2.8 (m, 4H, CH$_2$ and 2 cyclopentene-H); 3.1-4.2 (m, 6H, 4 cyclopentene-H and SCH$_2$); 4.53 (t, J=6 Hz, OCH$_2$); 5.1-6.3 (m, 4H, CH$_2$Py and 2 lactam-H); 7.42 (s, 1H, thiazole); 7.4-8.5 ppm (m, 3H, Py).

EXAMPLE 279

3-[(2,3-Cyclopenteno-1-pyridinium)]-methyl-7-[2-syn-ethoxyimino-2-(2-amino-5-chlorothiazol-4-yl)-acetamido]-ceph-3-em-4-carboxylate Colorless solid, yield 16% of theory.

$^1$H-NMR: (CF$_3$CO$_2$D): δ=1.42 (t, J=7 Hz, 3H, CH$_2$CH$_3$); 2.2-2.8 (m, 2 cyclopentene-H); 3.1-3.85 (m, 6H, 4 cyclopentene-H and SCH$_2$); 4.50 (q, J=7 Hz, 2H, CH$_2$CH$_3$); 5.15-6.25 (m, 4H, CH$_2$Py and 2 lactam-H); 7.6-8.7 (m, 3H, Py).

EXAMPLE 280

3-[(4-Cyclopropyl-1-pyridinium)-methyl]-7-[2-(2-amino-5-chlorothiazol-4-yl)-2-syn-methoxyimino-acetamido]-ceph-3-em-4-carboxylate Colorless solid, yield 45% of theory.

$^1$H-NMR: (CF$_3$CO$_2$D): δ=1.03-2.55 (m,5H, cyclopropyl); 3.37 and 3.81 (AB, J=18 Hz, 2H, SCH$_2$); 4.22 (s,3H,OCH$_3$); 5.03-6.25 (m,4H,CH$_2$Py and 2 lactam-H); 7.56 and 8.64 ppm (AA', BB', J=7 Hz, 4H,Py).

EXAMPLE 281

3-[(2,3-Cyclopenteno-1-pyridinium)-methyl]-7-[2-syn-ethoxyimino-2-(2-aminothiazol-4-yl)-acetamido]-ceph-3-em-4-carboxylate Colorless solid, yield 57% of theory.

$^1$H-NMR: (CF$_3$CO$_2$D): δ=1.43 (t,J=7 Hz, 3H, CH$_2$CH$_3$); 2.2-2.8 (m,2 cyclopentene-H); 305-3.94 (m, 6H, 4 cyclopentene-H and SCH$_2$); 4.51 (q, J=7 Hz, 2H, CH$_2$, CH$_3$); 5.05-6.26 (m,4H, CH$_2$Py and 2 lactam-H); 7.42 (s, 1H, thiazole); 7.5-8.75 (m,3H, Py).

We claim:

1. A cephem compound of the formula or a physiologically acceptable acid addition salt thereof, wherein R$^1$ is hydrogen or chlorine, OR$^2$ is in the syn-position and R$^2$ is C$_1$-C$_6$-alkyl, and A is a fused bicyclic ring substituent containing pyridinium to which is fused a ring of a di- to decamethylene or a ring of di- to deca-methylene which is mono-substituted by C$_1$-C$_6$-alkyl.

2. A cephem compound as in claim 1 or a physiologically acceptable acid addition salt thereof, wherein R$^1$ is hydrogen, OR$^2$ is in the syn-position and R$^2$ is methyl or ethyl, and A is pyridinium fused to a ring of trimethylene or tetramethylene.

3. A cephem compound as in claim 2 or a physiologically acceptable acid addition salt thereof, wherein A is pyridinium fused to a ring of trimethylene.

4. A cephem compound as in claim 3 or a physiologically acceptable acid addition salt thereof, wherein R$^2$ is methyl.

5. 7-[2-(2-Aminothiazol-4-yl)-2-syn-methoxyiminoacetamido]-3-[(2,3-cyclopenteno-1-pyridinium)-methyl]-ceph-3-em-4-carboxylate or a physiologically acceptable salt thereof.

6. 7-[2-(2-Aminothiazol-4-yl)-2-syn-methoxyiminoacetamido]-3-[(3,4-cyclopenteno-1-pyridinium)-methyl]-ceph-3-em-4-carboxylate or a physiologically acceptable salt thereof.

7. 7-[2-(2-Aminothiazol-4-yl)-2-syn-methoxyiminoacetamido]-3-[(5,6,7,8-tetrahydro-1-quinolinium)-methyl]-ceph-3-em-4-carboxylate or a physiologically acceptable salt thereof.

8. 7-[2-(Aminothiazol-4-yl)-2-syn-methoxyiminoacetamido]-3-[(3,4-cyclohexeno-1-pyridinium)-methyl]-ceph-3-em-4-carboxylate or a physiologically acceptable salt thereof.

* * * * *